United States Patent [19]

Coates et al.

[11] Patent Number: 5,360,800
[45] Date of Patent: * Nov. 1, 1994

[54] TETRAHYDRO-1H-PYRIDO[4,3-B]INDOL-1-ONE DERIVATIVES

[75] Inventors: Ian H. Coates, Hertford; Peter C. North; Alexander W. Oxford, both of Royston, all of England

[73] Assignee: Glaxo Group Limited, London, England

[*] Notice: The portion of the term of this patent subsequent to Feb. 2, 2010 has been disclaimed.

[21] Appl. No.: 741,570

[22] Filed: Aug. 7, 1991

Related U.S. Application Data

[63] Continuation of Ser. No. 602,771, Oct. 24, 1990, abandoned, which is a continuation of Ser. No. 239,626, Sep. 2, 1988, abandoned.

[30] Foreign Application Priority Data

Sep. 3, 1987 [GB] United Kingdom ................ 8720695
Aug. 15, 1988 [GB] United Kingdom ................ 8819382

[51] Int. Cl.[5] ................ C07D 401/06; C07D 471/04; A61K 31/44; A61K 31/55
[52] U.S. Cl. ................................ 514/215; 514/292; 540/524; 546/86; 546/87
[58] Field of Search ................ 546/85, 86, 87; 540/524; 514/292, 215

[56] References Cited

U.S. PATENT DOCUMENTS 4,636,563 1/1987 Abou-Gharbia ................ 546/87
4,695,578 9/1987 Coates et al. ................ 514/397

(List continued on next page.)

FOREIGN PATENT DOCUMENTS

238411A1 9/1987 European Pat. Off. .
39-20857 9/1964 Japan .
2180535B 4/1987 United Kingdom .

OTHER PUBLICATIONS

Fozard, *TIPS*, 8, Dec. 1987, pp. 501–506.
King et al., *Drugs of the Future*, 14(9), 1989, pp. 875–889.
Abou-Gharbia et al., *J. Med. Chem.*, 1987, 30, 1818–1823.

*Primary Examiner*—Alan L. Rotman
*Attorney, Agent, or Firm*—Bacon & Thomas

[57] ABSTRACT

The invention relates to tricyclic lactams of the general formula (I)

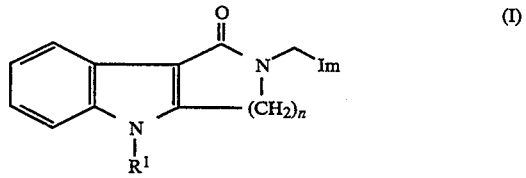

wherein Im represents an imidazolyl group of the formula:

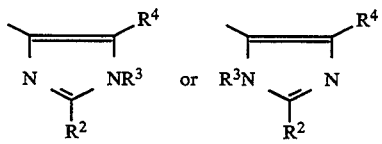

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkylC$_{1-4}$alkyl, phenyl, phenyl $C_{1-3}$alkyl, phenylmethoxymethyl, phenoxyethyl or phenoxymethyl, one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl $C_{1-3}$alkyl group, and each of the other two groups, which may be the same or different, represents a hydrogen atom or a $C_{1-6}$alkhyl group;

n represents 2 or 3; and physiologically acceptable salts and solvates thereof.

The compounds are potent and selective antagonists of the effect of 5-HT at 5-HT$_3$ receptors and are useful, for example, in the treatment of psychotic disorders, anxiety, and nausea and vomiting.

35 Claims, No Drawings

U.S. PATENT DOCUMENTS

| | | | |
|---|---|---|---|
| 4,725,615 | 2/1988 | Coates et al. | 514/397 |
| 4,739,072 | 4/1988 | Oxford et al. | 548/336 |
| 4,749,718 | 6/1988 | Coates et al. | 514/397 |
| 4,754,038 | 6/1988 | Abou-Gharbia | 546/87 |
| 4,798,896 | 1/1989 | Abou-Gharbia et al. | 546/87 |
| 4,808,581 | 2/1989 | Oxford et al. | 514/212 |
| 4,814,344 | 3/1989 | Humber et al. | 514/397 |
| 4,822,881 | 4/1989 | Coates et al. | 540/603 |
| 4,985,422 | 1/1991 | North et al. | 514/215 |
| 5,183,820 | 2/1993 | Coates et al. | 514/292 |

TETRAHYDRO-1H-PYRIDO[4,3-B]INDOL-1-ONE DERIVATIVES

This application is a continuation of application Ser. No. 07/602,771, filed Oct. 24, 1990, abandoned which is a continuation of application Ser. No. 07/239,626, filed Sep. 2, 1988, now abandoned.

This invention relates to lactam derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as 5-HT$_3$receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at 5-HT$_3$ receptors have been described previously.

Thus for example published UK Patent Specification No. 2153821A and published European Patent Specifications Nos. 191562, 219193 and 210840 disclose 3-imidazolylmethyltetrahydrocarbazolones which may be represented by the general formula:

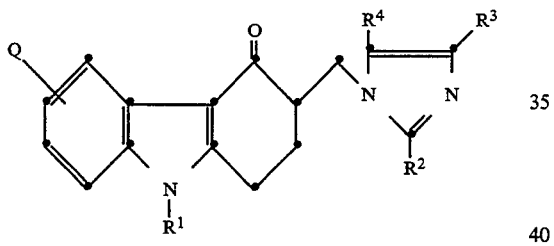

wherein R$^1$ represents a hydrogen atom or a group selected from C$_{1-10}$alkyl, C$_{3-6}$ alkenyl, C$_{3-10}$ alkynyl, C$_{3-7}$ cycloalkyl, C$_{3-7}$cycloalkylC$_{1-4}$alkyl, phenyl or phenylC$_{1-3}$alkyl, and in the case where Q represents a hydrogen atom, R$^1$ may also represent —CO$_2$R$^5$, —COR$^5$, —CONR$^5$R$^6$ or —SO$_2$R$^5$ (wherein R$^5$ and R$^6$, which may be the same or different, each represents a hydrogen atom, a C$_{1-6}$ alkyl or C$_{3-7}$cycloalkyl group, or a phenyl or phenylC$_{1-4}$alkyl group, in which the phenyl group is optionally substituted by one or more C$_{1-4}$ alkyl, C$_{1-4}$alkoxy or hydroxy groups or halogen atoms, with the proviso that R$^5$ does not represent a hydrogen atom when R$^1$ represents a group —CO$_2$R$^5$ or —SO$_2$R$^5$);

one of the groups represented by R$^2$, R$^3$ and R$^4$ is a hydrogen atom or a C$_{1-6}$ alkyl, C$_{3-7}$ cycloalkyl, C$_{2-6}$alkenyl, or phenylC$_{1-3}$alkyl group, and each of the other two groups, which may be the same or different, represents a hydrogen atom or a C$_{1-6}$ alkyl group;

Q represents a hydrogen atom or a halogen atom or a hydroxy, C$_{1-4}$alkoxy, phenylC$_{1-3}$alkoxy or C$_{1-6}$ alkyl group or a group —NR$^7$R$^8$ or —CONR$^7$R$^8$ (wherein R$^7$ and R$^8$, which may be the same or different, each represents a hydrogen atom or a C$_{1-4}$ alkyl or C$_{3-4}$ alkenyl group, or together with the nitrogen atom to which they are attached form a saturated 5 to 7 membered ring);

and physiologically acceptable salts and solvates thereof.

We have now found a noval group of compounds which differ in structure from those described previously, and which are potent antagonists of the effect of 5-HT at 5-HT$_3$ receptors.

The present invention provides a tricyclic lactam of the general formula (I):

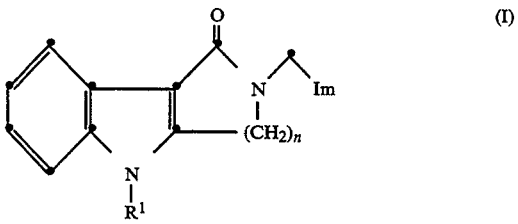

wherein Im represents an imidazolyl groups of the formula:

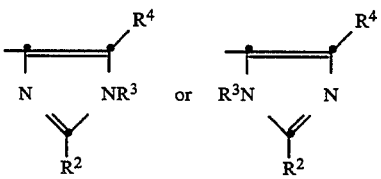

and R$^1$ represents a hydrogen atom or a group selected from C$_{1-6}$alkyl, C$_{3-6}$alkenyl, C$_{3-10}$alkynyl, C$_{3-7}$cycloalkyl, C$_{3-7}$cycloalkylC$_{1-4}$ alkyl, phenyl, phenylC$_{1-3}$alkyl, phenylmethoxymethyl, phenoxyethyl, phenoxymethyl, —CO$_2$R$^5$, —COR$^5$, —CONR$^5$R$^6$ or —SO$_2$R$^5$ (wherein R$^5$ and R$^6$, which may be the same or different, each represents a hydrogen atom, a C$_{1-6}$ alkyl or C$_{3-7}$ cycloalkyl group, or a phenyl or phenylC$_{1-4}$alkyl group, in which the phenyl group is optionally substituted by one or more C$_{1-4}$ alkyl, C$_{1-4}$ alkoxy or hydroxy groups or halogen atoms, with the proviso that R$^5$ does not represent a hydrogen atom when R$^1$ represents a group —CO$_2$R$^5$ or —SO$_2$R$^5$);

one of the groups represented by R$^2$, R$^3$ and R$^4$ is a hydrogen atom or a C$_{1-6}$alkyl, C$_{3-7}$cycloalkyl, C$_{3-6}$alkenyl, phenyl or phenylC$_{1-3}$alkyl group, and each of the other two groups, which may be the same or different, represents a hydrogen atom or a C$_{1-6}$ alkyl group;

n represents 2 or 3; and physiologically acceptable salts and solvates thereof.

According to one aspect, the invention provides compounds of formula (I) wherein R$^1$ represents a hydrogen atom or a group selected from C$_{1-6}$ alkyl, C$_{3-6}$ alkenyl, C$_{3-10}$ alkynyl, C$_{3-7}$cycloalkyl, C$_{3-7}$cycloalkylC$_{1-4}$ alkyl, phenyl or phenylC$_{1-3}$ alkyl (n and Im being as defined in formula (I)).

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonate), phosphates, acetates, citrates, succinates, tartrates, fumarates and maleates. The solvents may, for example, be hydrates.

All optical isomers of compounds of general formula (I) and their mixtures including the racemic mixtures thereof, and all the geometric isomers of compounds of formula (I), are embraced by the invention.

Referring to the general formula (I), an alkyl group may be a straight chain or branched chain alkyl group, for example, methyl, ethyl, n-propyl, prop-2-yl, n-butyl, but-2-yl, 2-methylprop-2-yl, n-pentyl, pent-3-yl or n-hexyl, A $C_{3-6}$ alkenyl group may be, for example, a propenyl or butenyl group. When $R^1$ represents a $C_{3-6}$alkenyl or $C_{3-10}$alkynyl group, or $R^3$ represents a $C_{3-6}$alkenyl group, or $R^7$ or $R^8$ represents a $C_{3-4}$alkenyl group, the double or triple bond may not be adjacent to the nitrogen atom. A phenyl$C_{1-3}$alkyl group may be, for example, a benzyl, phenethyl or 3-phenylpropyl group. A $C_{3-7}$cycloalkyl group may be, for example, a cyclopropyl, cyclobutyl, cyclopentyl, cyclohexyl or cycloheptyl group.

A preferred class of compounds of formula (I) is that wherein $R^1$ represents a hydrogen atom or a $C_{1-6}$ alkyl (e.g. methyl, ethyl, n-propyl, prop-2-yl), $C_{3-4}$ alkenyl (e.g. prop-2-enyl), $C_{3-4}$ alkynyl (e.g. prop-2-ynyl), $C_{5-6}$cycloalkyl (e.g. cyclopentyl), $C_{5-6}$cycloalkylmethyl (e.g. cyclopentylmethyl), phenyl$C_{1-2}$ alkyl (e.g. benzyl), phenylmethoxymethyl, N,N-di$C_{1-3}$alkylcarboxamido (e.g. N,N-dimethylcarboxamido) or $C_{1-3}$alkylsulphonyl (e.g. methylsulphonyl) group. More preferably $R^1$ represents a $C_{1-4}$ alkyl (e.g. methyl or n-propyl), $C_{3-4}$alkynyl (e.g. prop-2-ynyl), $C_{5-6}$cycloalkyl (e.g. cyclopentyl), $C_{5-6}$cycloalkylmethyl (e.g. cyclopentylmethyl), phenyl$C_{1-2}$ alkyl (e.g. benzyl), phenylmethoxymethyl, or N,N-di$C_{1-3}$alkylcarboxamido (e.g. N,N-dimethylcarboxamido) group.

Another preferred class of compounds of formula (I) is that wherein $R^2$ represents a hydrogen atom or a $C_{1-3}$ alkyl (e.g. methyl) group, more preferably a hydrogen atom.

Another preferred class of compounds of formula (I) is that wherein $R^3$ represents a hydrogen atom or a $C_{1-3}$ alkyl (e.g. methyl) group, more preferably a hydrogen atom.

A further preferred class of compounds of formula (I) is that wherein $R^4$ represents a hydrogen atom or a $C_{1-3}$ alkyl (e.g. methyl or n-propyl) group. Most preferably $r^4$ represents a methyl group.

When $R^2$ and $R^3$ represent hydrogen atoms, $R^4$ is preferably $C_{1-6}$alkyl, $C_{3-7}$ cycloalkyl, $C_{3-6}$ alkenyl or phenyl$C_{1-3}$alkyl, more particularly $C_{1-6}$ alkyl.

A further preferred class of compounds of formula (I) is that wherein n represents 2.

A preferred group of compounds of formula (I) is that wherein $R^1$ represents a hydrogen atom or a $C_{1-4}$ alkyl, $C_{3-4}$alkenyl, $C_{3-4}$alkynyl, $C_{5-6}$cycloalkyl, $C_{5-6}$cycloalkylmethyl, phenyl$C_{1-2}$ alkyl, phenylmethoxymethyl, N,N-di$C_{1-3}$alkylcarboxamido or $C_{1-3}$alkylsulphonyl group; $R^2$ represents a hydrogen atom; and $R^3$ and $r^4$ each represent a hydrogen atom or a $C_{1-3}$ alkyl group.

A particularly preferred group of compounds of formula (I) is that wherein $R^1$ represents a methyl, n-propyl, prop-2-ynyl, cyclopentyl, cyclopentylmethyl, benzyl or N,N-dimethylcarboxamido group; $R^2$ and $R^3$ each represent a hydrogen atom; and $R^4$ represents a methyl group.

Within the above preferred and particularly preferred groups of compounds, an especially important group of compounds is that in which n represents 2.

Preferred compounds according to the invention are:

2,3,4,5-tetrahydro-5-methyl-2-[(5-methyl-1H-imidazol-4-yl)methyl]-1H-pyrido[4,3-b]indol-1-one;

2,3,4,5-tetrahydro-5-(phenylmethyl)-2-[(5-methyl-1H-imidazol-4-yl)-methyl]-1H-pyrido[4,3-b]indol-1-one;

5-cyclopentyl-2,3,4,5-tetrahydro-2-[(5-methyl-1H-imidazol-4yl)-methyl]-1H-pyrido[4,3-b]indol-1-one;

2,3,4,5-tetrahydro-2[(5-methyl-1H-imidazol-4-yl)methyl]-5-propyl-1H-pyrido[4,3-b]indol-1-one;

5-(cyclopentylmethyl)-2,3,4,5-tetrahydro-2-[(5-methyl-1H-imidazol-4-yl) methyl]-1H-pyrido[4,3-b]indol-1-one;

3,4,5,6-tetrahydro-6-methyl-2-[(5-methyl-1H-imidazol-4-yl)methyl]-azepino[4,3-b]indol-1(2H)-one;

2,3,4,5-tetrahydro-N,N-dimethyl-2-[(5-methyl-1H-imidazol-4yl)-methyl]-1-oxo-5H-pyrido[4,3-b]indole-5-carboxamide;

2,3,4,5-tetrahydro-2-[(5-methyl-1H-imidazol-4-yl)methyl]-5-(2-propynyl)-1H-pyrido[4,3-b]indol-1-one;

and their physiologically acceptable salts and solvates.

The potent and selective antagonism of 5HT at 5-HT$_3$ receptors by compounds of the invention has been demonstrated by their ability to inhibit 3-(5-methyl-1H-imidazol-4yl)-1-[1-(methyl-t$_3$)-1H-indol-3yl]-1-propanone binding in rat entorhinal cortex homogenates (following the general procedure described by G. Kilpatrick et al. in Nature, 1987, 330, 746), and/or by their ability to inhibit the 5-HT-induced depolarisation of the rate isolated vagus nerve preparation.

In addition to their activity as potent and selective antagonists of 5-HT at 5-HT$_3$ receptors, certain compounds according to the invention have the advantage of an extended duration of action.

a particularly preferred compound on account of both its potency and duration of action is 2,3,4,5-tetrahydro-5-methyl-2-[(5-methyl-1H-imidazol-4-yl)methyl]-1H-pyrido[4,3-b]indol-1-one and its physiologically acceptable salts and solvates. Preferred salts of this compound are the hydrochloride and maleate.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; or pain, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparation for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterily pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intra nasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine, 1-methyl-5-[[3-[3-(1-piperidinylmethyl)phenoxy]propyl]amino]-1H-1,2,4-triazole-3-methanol, cimetidine, famotidine, nizatidine or roxatidine) or $H^+K^+$ATPase inhibitors (e.g. omeprazole).

A proposed dose of the compounds of the invention for administration to man (of approximately 70 kg body weight) is 0.001 to 100 mg, preferably 0.01 to 50 mg, more preferably 0.1 to 20 mg of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups $R^1$, n, and Im are as defined for compounds of general formula (I) unless otherwise stated.

According to a first general process (A), a compound of general formula (I) may be prepared by alkylating a compound of formula (II):

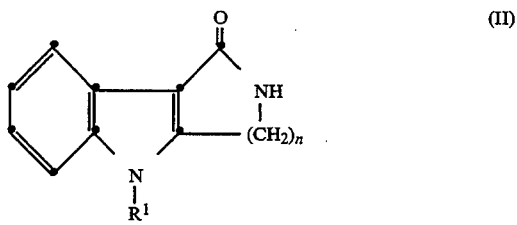

(II)

with a compound of formula (III):

LCH$_2$-Im (III)

or a protected derivative thereof, wherein L represents a leaving atom or group, such as a halogen atom (e.g. chlorine, bromine or iodine), or an acyloxy group (e.g. trifluoroacetyloxy or acetoxy), or a sulphonyloxy group (e.g. trifluoromethanesulphonyloxy, p-toluenesulphonyloxy or methanesulphonyloxy), followed wherein necessary by removal of any protecting groups. L is preferably a halogen atom (e.g. a chlorine atom).

The reaction may be carried out in an inert solvent such as an ether (e.g. dimethoxyethane, diglyme or tetrahydrofuran), a substituted amide (e.g. dimethylformamide or N-methylpyrrolidone), an aromatic hydrocarbon (e.g. toluene), a ketone (e.g. acetone), or dimethyl sulphoxide, at a temperature between ambient and 100° C., in the presence of a base. Suitable bases include alkali metal hydrides (e.g. sodium hydride), alkali metal carbonates (e.g. sodium carbonate), alkali metal amides (e.g. sodium amide), alkali metal alkoxides (e.g. potassium t-butoxide) or alkali metal hydroxides (e.g. sodium or potassium hydroxide).

According to another general process (B), a compound of general formula (I) wherein n represents 2, may be prepared by hydrogenation of a compound of formula (IV):

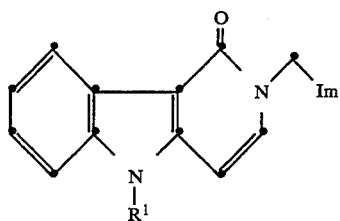

(IV)

or a protected derivative thereof, followed where necessary by removal of any protecting groups.

Hydrogenation according to general process (B) may be effected using conventional procedures, for example using hydrogen in the presence of a noble metal catalyst (e.g. palladium, Raney nickel, platinum or rhodium). The catalyst may be supported on, for example, charcoal or alumina, or alternatively a homogeneous catalyst such as tris(triphenylphosphine)rhodium chloride may be used. The hydrogenation will generally be effected in a solvent such as an alcohol (e.g. methanol or ethanol), an ether (e.g. dioxan), or an ester (e.g. ethyl acetate), or in a mixture of an alcohol and either a hydrocarbon (e.g. toluene) or a halogenated hydrocarbon (e.g. dichloromethan), at a temperature in the range −20° to +100° C., and at a pressure of from 1 to 10 atmospheres.

According to another general process (C), a compound of general formula (I) may be prepared by cyclising a compound of formula (V):

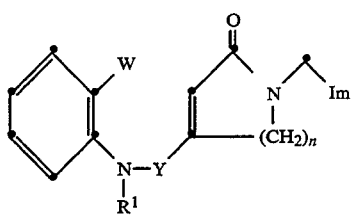

(V)

wherein W represents a hydrogen atom and Y represents the group NH, or W represent a halogen atom and Y represents a bond, or a salt or protected derivative thereof, followed where necessary by removal of any protecting groups.

According to one embodiment (a) of process (C), the reaction is effected with a compound of formula (V) wherein W represents a hydrogen atom and Y represents the group NH, and the cyclisation may be carried out in aqueous or non-aqueous media, in the presence of an acid catalyst.

It will be appreciated that these compounds of formula (V) may exist in the corresponding enol hydrazone tautomeric form.

When an aqueous medium is employed this may be water or a mixture of water and a organic solvent such as an alcohol (e.g. methanol, ethanol or isopropanol) or an ether (e.g. dioxan or tetrahydrofuran). The acid catalyst may be, for example, an inorganic acid such as concentrated hydrochloric or sulphuric acid. In some cases the acid catalyst may also act as the reaction solvent. In an anhydrous reaction medium, which may comprise one or more alcohols or ethers (e.g. as described above), carboxylic acids (e.g. acetic acid) or esters (e.g. ethyl acetate), the acid catalyst may alternatively by a Lewis acid such as boron trifluoride, zinc chloride or magnesium chloride. The cyclisation reaction may conveniently be carried out at temperatures of from 20° to 200° C., preferably 20° to 125° C.

Alternatively the cyclisation according to embodiment (a) of process (C) may be carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethyl ether and chloroform according to the method described in 'Reagents for Organic Synthesis', (Fieser and Fieser, John Wiley and Sons, 1967).

According to another embodiment (b) of process (C), the reaction is effected with a compound of formula (V) wherein W represents a halogen atom, for example, a chlorine atom or, more preferably, a bromine or iodine atom, Y represents a bond, and the cyclisation is effected photochemically.

The reaction may conveniently be effected by irradiating with a mercury lamp, preferably a medium or high pressure mercury lamp. Suitable solvents include nitriles (e.g. acetonitrile), chlorinated hydrocarbons (e.g. carbon tetrachloride) and cyclic ethers (e.g. tetrahydrofuran or dioxan) and mixtures thereof. The reaction may conveniently be effected in the presence of abase such as a tertiary amine (e.g. triethylamine).

According to another general process (D), a compound of general formula (I) wherein $R^3$ represents a hydrogen atom, may be prepared by the reaction of a compound of formula (VI):

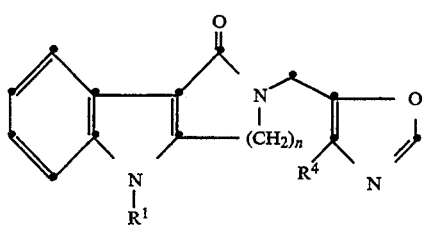

(VI)

or a protected derivative thereof, with formamide, at a temperature in the range of 150° to 200° C., followed where necessary by removal of any protecting groups.

According to another general process (E), a compound of general formula (I) may be prepared by reacting a compound of formula (VII):

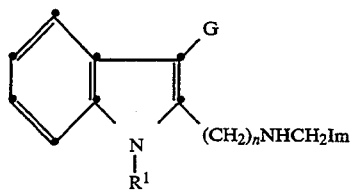

(VII)

wherein G represents a hydrogen atom, or a protected derivative thereof, with phosgene in the presence of a Lewis acid; or by reacting a compound of formula (VII) wherein G represents an iodine or a bromine atom, or a protected derivative thereof, with carbon monoxide in the presence of a palladium (II) salt, followed where necessary by removal of any protecting groups.

According to one embodiment of process (E), a compound of formula (VII), wherein G represents a hydrogen atom, is reacted with phosgene in the presence of a Lewis acid such as anhydrous aluminium trichloride or stannic chloride. The reaction may conveniently by effected in an inert solvent such as an aromatic hydrocarbon (e.g. toluene) or a halogenated hydrocarbon (e.g. dichloromethane), or mixtures thereof, and at a temperature between ambient and 100° C.

According to another embodiment of process (E), a compound of formula (VII), wherein G represents an iodine or a bromine atoms, is reacted with carbon monoxide in the presence of a palladium (II) salt (e.g. palladium acetate or palladium chloride) and preferably in the presence of triphenylphosphine. The reaction may conveniently be effected in a solvent such as a tertiary amine (e.g. tri-n-butylamine), optionally in the presence of a co-solvent such as an ether (e.g. tetrahydrofuran) or an aromatic hydrocarbon (e.g. toluene), at a temperature in the range 100° to 150° C., and at atmospheric pressure.

According to another general process (F), a compound of general formula (I) may be converted into another compound of formula (I) using conventional techniques. Such conventional techniques include hydrogenation, alkylation and acylation using protection and deprotection where necessary.

Thus, according to one embodiment of the interconversion process (F), hydrogenation may be used to convert an alkenyl or an alkynyl substituent into an alkyl substituent, or an alkynyl into an alkenyl substituent. Hydrogenation may also be used to replace a phenylmethoxymethyl group by a hydrogen atom. Hydrogenation according to general process (F) may be effected using conventional procedures, for example, using hydrogen in the presence of a catalyst, as described above in general process (B).

The term 'alkylation' according to general process (F) includes the introduction of groups such as cycloalkyl, alkenyl or phenalkyl groups.

Thus, for example, a compound of formula (I) in which $R^1$ represents a $C_{1-6}$ alkyl, $C_{3-6}$ alkenyl, $C_{3-10}$ alkynyl, $C_{3-7}$ cycloalkyl, $C_{3-7}$cycloalkyl$C_{1-4}$ alkyl, phenyl $C_{1-3}$ alkyl, phenylmethoxymethyl, phenoxyethyl or phenoxymethyl group may be prepared by alkylating a compound of formula (I) in which $R^1$ represents a hydrogen atom, or a compound in which $R^3$ represents a $C_{1-6}$alkyl, $C_{3-7}$cycloalkyl, $C_{3-6}$alkenyl or phenyl$C_{1-3}$alkyl group may be prepared by alkylating the corresponding compound of formula (I) in which $R^3$ represents a hydrogen atom, using conventional procedures, for example as described in published may be effected using an appropriate alkylating agent of formula $R^7Z$ (where $R^7$ is the group to be introduced and Z is a leaving atom or group), preferably in the presence of a base.

According to another embodiment of general process (F), a compound of formula (I) wherein $R^1$ represents $-CO_2R^5$, $-COR^5$, $-CONR^5R^6$ or $-SO_2R^5$ may be prepared by acylating or sulphonylating as appropriate, a compound of formula (I) wherein $R^1$ represents a hydrogen atom. The acylation/sulphonylation reactions may be effected using an appropriate acylating-/sulphonylating agent according to conventional procedures, for example, as described in published European Patent Specification No. 210840.

It should be appreciated that in the above transformations it may be necessary or desirable to protect any sensitive groups in the molecule of the compound in question to avoid undesirable side reactions. For example, it may be necessary to protect the indole and/or imidazole nitrogen atoms, for example with an arylmethyl (e.g. trityl), arylmethoxymethyl (e.g. phenylmethoxymethyl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group.

Thus according to another general process (G), a compound of general formula (I) may be prepared by the removal of any protecting groups from a protected form of a compound of formula (I). Deprotection may be effected using conventional techniques such as those described in 'Protective Groups in Organic Synthesis' by T. S. Greene (John Wiley and sons, 1981).

For example, an arylmethoxymethyl N-protecting group may be cleaved by hydrogenolysis in the presence of a catalyst (e.g. palladium on charcoal). A trityl group may be cleaved by acid hydrolysis (e.g. using dilute hydrochloric or acetic acid). An alkoxyalkyl group may be removed using a mineral acid (e.g. dilute hydrochloric or hydrobromic acid). An acyl group may be removed by hydrolysis under acidic or basic conditions (e.g. using hydrogen bromide, dilute hydrochloric acid or sodium hydroxide). A sulphonyl group may also be removed by alkaline or acidic hydrolysis, and an N, N-dimethylaminosulphonyl group may also be removed (e.g. from an imidazole nitrogen atom) by photolysis.

Compounds of formula (II) may be obtained by a Beckmann rearrangement of an oxime of formula (VIII):

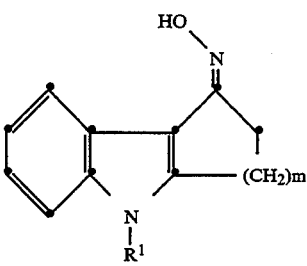

(VIII)

wherein m represents 1 or 2, or a protected derivative thereof. The Beckmann rearrangement may be effected using conventional methods, for example by using an acid (e.g. polyphosphoric or sulphuric acid, or a mixture of hydrochloric acid, acetic anhydride and acetic acid) in an inert solvent such as an ether (e.g. dioxan), an amide (e.g. dimethylformamide) or a hydrocarbon (e.g. toluene or cyclohexane), at an elevated temperature of, for example, 50° to 120° C. Alternatively, the hydroxy group of the oxime of formula (VIII), may be converted into a leaving group such as a chloride (using, for example, phosphorus pentachloride) or a hydrocarbylsulphonate (e.g. a mesylate or a tosylate) or a trifluoroacetate group (using conventional acylation methods). Subsequent heating at a temperature of, for example, 20° to 150° C., in an inert solvent as described above, gives a compound of formula (II).

Compounds of formula (VIII) may be prepared from the corresponding tricyclic ketone of formula (IX):

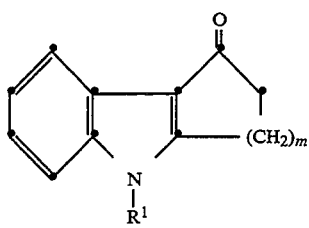

(IX)

wherein m represents 1 or 2, or a protected derivative thereof using conventional methods, for example by using hydroxylamine hydrochloride in a solvent such as pyridine.

Compounds of formula (IV) may be prepared, for example, by reacting a compound of formula (X):

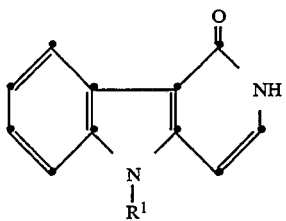

(X)

or a protected derivative thereof, with a compound of formula (III) wherein L is as defined previously, or a protected derivative thereof, using the conditions described in process (A).

Compounds of formula (X) may be prepared by heating a compound of formula (II) wherein n represents 2, with a noble metal catalyst such as palladium, palladium oxide, platinum or nickel, at a temperature of, for example, 300° to 350° C. The catalyst may be supported on, for example, charcoal or alumina, and the reaction may optionally be carried out in the presence of an inert solvent such as an aromatic hydrocarbon (e.g. p-cymene)

Compounds of formula (V) wherein W represents a hydrogen atom and Y represents the group NH may be prepared by the reaction of a compound of formula (XI):

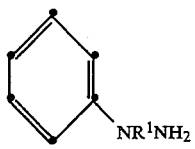

(XI)

or a salt thereof, with a compound of formula (XII):

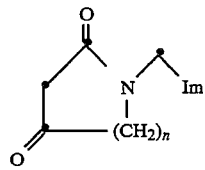

(XII)

or a protected derivative thereof, in a suitable solvent such as an aqueous alcohol (e.g. methanol), and at a temperature of, for example, from 20° to 100° C.

A protected derivative of a compound of formula (XII) may for example have the keto carbonyl group protected (e.g. as an enol ether). It will be appreciated that when a compound of formula (XII) is used in which the keto carbonyl group is protected, it may be necessary to remove the protecting group in order for reaction to occur with the compound of formula (XI). Deprotection may be carried out by conventional methods, for example by acidic hydrolysis (e.g. using dilute sulphuric or hydrochloric acid). If desired, deprotection may be effected in situ.

Compounds of formula (XII) may be prepared, for example, by reacting a compound of formula (XIII):

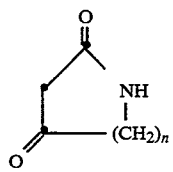

(XIII)

or a protected derivative thereof, with a compound of formula (III) wherein L is as defined previously, or a protected derivative thereof, using the conditions described in process (A).

Compounds of formula (V) wherein W represents a halogen atom and Y represents a bond may be prepared, for example, by reacting a compound of formula (XIV):

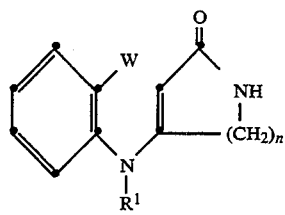

(XIV)

wherein W represents a halogen atom, or a protected derivative thereof, with a compound of formula (III) wherein L is as defined previously, or a protected derivative thereof, using the conditions described in process (A).

Compounds of formula (XIV) may be prepared by reacting a compound of formula (XV):

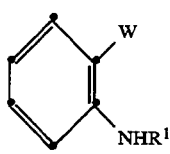

with a compound of formula (XIII), at an elevated temperature.

Compounds of formula (VI) may be prepared, for example, by reacting a compound of formula (II), or a protected derivative thereof, with a compound of formula (XVI):

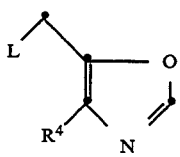

wherein L is as defined previously, using the conditions described in process (A).

Compounds of formula (VII) wherein G represents a halogen atom may be prepared, for example by reacting a compound of formula (VII) wherein G represents a hydrogen atom, or a protected derivative thereof, with an appropriate halogen and alkali metal halide (e.g. iodine and potassium iodide), in a suitable solvent such as an aqueous alcohol (e.g. aqueous ethanol).

Compounds of formula (VII) wherein G represents a hydrogen atom may be prepared, for example, by reacting a compound of formula (XVII):

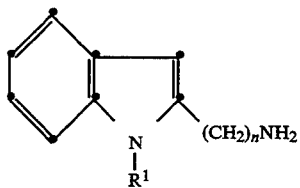

or a protected derivative thereof, with a compound of formula (III) wherein L is as defined previously, or a protected derivate thereof, using the conditions described in process (A).

Compounds of formula (III) and protected derivative thereof, are either known, or may be prepared, for example, by the methods described in German Offenlegungsschrift No. 3740352.

Compounds of formula (IX) may be prepared, for example, by the method or methods analogous to that described by H. Iida et al. in *J. Org. Chem.*, 1980, 45, 2938.

Compounds of formulae (XI), (XIII), (XV), (XVI) and (XVII) are either known, or may be prepared from known compounds by conventional procedures.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran).

Physiologically acceptable salts may also be prepared from other salts, including other physiologically acceptable salts, of the compounds of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

The methods described above for preparing the compounds of the invention may be used for the introduction of the desired groups at any stage in the stepwise formation of the required compounds, and it will be appreciated that these methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in ° C. Thin layer chromatography (t.l.c.) was carried out on silica, and flash column chromatography (FCC) on silica (Merck 9385). solvent System A as used for chromatography denotes dichloromethane:ethanol:0.88 ammonia solution. Organic extracts were dried, where indicated, over magnesium sulphate or sodium sulphate. The following abbreviations are used: DMF - dimethylforamide; THG - tetrahydrofuran; DME - dimethoxyethane. $^1$H-N,m.r. spectra were obtained at 250 MHz for dilute solutions in $d_6$-dimethyl sulphoxide.

Intermediate 1

4-(Chloromethyl)-1-(triphenylmethyl)-1H-imidazole

Thionyl chloride (0.82 g) was added over 1 min. to a stirred suspension of 1-(triphenylmethyl)-1H-imidazole-4-methanol (1.3 g) in a mixture of dichloromethane (50 ml) and DMF (1.0 ml) at 23°. The solution so obtained was stirred for 15 min. and extracted with 8% sodium bicarbonate solution (80 ml). The organic phase was washed with water (50 ml), dried and evaporated to give an oil which solidified. The solid was slurried in hexane and filtered to give the title compound (1.28 g), m.p. 139°–141°.

Intermediate 2

4-Formyl-N,N-dimethyl-5-propyl-1H-imidazole-1-sulphonamide

Demethylsulphamoyl chloride (0.67 ml) was added to a stirred solution of 5-propyl-1H-imidazole-4-carboxaldehyde (860 mg) and triethylamine (0.87 ml) in dry dichloromethane (10 ml) under nitrogen. The solution was heated at reflux for 24 h, allowed to cool, poured into water (50 ml) and extracted with dichloromethane (3×25 ml). The combined, dried organic extracts were evaporated to give an oil (1.9 g) which was purified by FCC eluting with ethyl acetate:hexane (1:1) to give the title compound (500 mg), m.p. 57°–58°.

Intermediate 3

4-(Hydroxymethyl)-N,N-dimethyl-5-propyl-1H-imidazole-1-sulphonamide

Sodium borohydride (139 mg) was added to a stirred solution of 4-formyl-N,N-dimethyl-5-propyl-1H-imidazole-1-sulphonamide (450 mg) in absolute ethanol (5 ml) under nitrogen. After 3 h the mixture was poured into water (30 ml) and extracted with dichloromethane (3×15 ml). The combined, dried organic extracts were evaporated to give a solid (425 mg) which was triturated with ether (2×10 ml) to give the title compound (350 mg), m.p. 86°–88°.

Intermediate 4

4-(Chloromethyl)-N,N-dimethyl-5-propyl-1H-imidazole-1-sulphonamide

A solution of thionyl chloride (0.12 ml) in dry dichloromethane (1.2 ml) was added dropwise to a cold (0°) stirred solution of 4-(hydroxymethyl)-N,N-dimethyl-5-propyl-1H-imidazole-1-sulphonamide (340 mg) in dry dichloromethane (7.5 ml) under nitrogen. After 1.5 h the solution was washed with 8% sodium bicarbonate solution (2×15 ml) and the aqueous phase was extracted with dichloromethane (2×10 ml). The combined organic extracts were washed with water (15 ml), dried and evaporated to give the title compound (180 ml) as an oil, t.l.c. (ethyl acetate) Rf 0.68.

Intermediate 5

3,4-Dihydro-4-methylcyclopent[b]indol-1(2H)-one oxime 3,4-Dihydro-4-methylcyclopent[b]indol-1(2H)-one (1.7 g) and hydroxylamine hydrochloride (1.925 g) in pyridine were heated at 60° for 18 h and cooled. The reaction mixture was evaporated in vacuo to a residue to which was added 8% sodium bicarbonate (150 ml). Extraction with ethyl acetate (300 ml) produced a suspension in the organic layer; this layer and associated solid was separated from the aqueous layer. The aqueous layer was re-extracted with ethyl acetate (250 ml). The combined organic extracts (and suspended solid) were evaporated to a residue, boiled with a mixture of ethanol (150 ml) and methanol (150 ml) and cooled to ca. 50°. The residue was adsorbed from this solution on to FCC silica and applied to an FCC column. Elution with ethyl acetate/3–10% methanol provided the title compound (1.69 g), m.p. 219°–224° (decomp.).

Intermediate 6

2,3,4,5-Tetrahydro-5-methyl-1H-pyrido[4,3-b]indol-1-one 3,4-Dihydro-4-methylcyclopent[b]indol-1(2H)-one oxime (1.53 g), polyphosphric acid (450 g) and dioxan (15 ml) were heated at 100°–120° for 2.2 h under nitrogen. The reaction mixture was cooled, and treated with 2N sodium carbonate solution (1 l). The suspension was extracted with ethyl acetate (4×400 ml) and the combined extracts were dried. Evaporation gave a solid (1.43 g) which was recrystallised from ethyl acetate/cyclohexane. This solid was purified by FCC, eluting with System A (200:10:1) to give a solid (1.26 g) which was recrystallised from ethanol to provide the title compound (960 mg), m.p. 234°–238°.

Intermediate 7

3,4,5,6,-Tetrahydro-6-methylazepino[4,3-b]indol-1(2H)-one 1,2,3,9-Tetrahydro-9-methyl-4H-carbazol-4-one oxime (24 g) and polyphosphoric acid (600 g) in dioxan (500 ml) were treated according to the method described for Intermediate 6. The solid (22 g) obtained by evaporation of the organic extracts was recrystallised from ethyl acetate (300 ml) to give a solid (19.2 g). This was purified by FCC eluting with System A (200:8:1) to give the title compound (5.5 g), m.p. 212°–215°.

Intermediate 8

5,6-Dihydro-4-(phenylamino)-1(2H)-pyridinone

A mixture of 2,4-dioxopiperidine (1.13 g) and aniline (930 mg) was heated at 120° under a stream of nitrogen for 15 min. The resultant solid was triturated with ether and filtered off to give the title compound (1.74 g), m.p. 235°–238°.

Intermediate 9

2,3,4,5-Tetrahydro-1H-pyrido[4,3-b]indol-1-one

A solution of 5,6-dihydro-4-(phenylamino)-1(2H)-pyridinone (1.5 g) and palladium acetate (150 mg) in dry DMF (50 ml) was treated with cupric acetate (3.2 g) and the resulting mixture was heated under nitrogen at 120°–130° for 1.5 h. The mixture was then concentrated in vacuo to give a solid which was triturated with 2N hydrochloric acid (250 ml). The acid was decanted, and the remaining solid was extracted with ethyl acetate for 18 h. The decanted acid was basified with 2N sodium hydroxide and extracted with ethyl acetate (3×100 ml). These organic extracts were combined with the previous ethyl acetate extracts and adsorbed onto silica. Purification by FCC eluting with System A (100:8:1) gave the title compound (874 mg), m.p. 212°–215°.

Intermediate 10

2,3,4,5-Tetrahydro-5-[(phenylmethoxy)methyl]-1H-pyrido[4,3-b]indol-1-one a solution of 2,3,4,5-tetrahydro-1H-pyrido[4,3-b]indol-1-one (1.12 g) in dry DMF (60 ml) was treated with sodium hydride (60% dispersion in oil; 480 mg) and the resulting mixture was stirred under nitrogen until effervescence ceased. The mixture was then cooled to 0° and benzyl (chloromethyl) ether (10% w/v solution in DMF; 0,835 ml) was added over 10 min. Stirring was continued for a further 5 min and then water (10 ml) was added. The reaction mixture was concentrated in vacuo to give an oil which was dissolved in ethyl acetate (100 ml) and washed with water (3×100 ml). The organic phase was dried and adsorbed onto FCC silica. Purification by FCC eluting with System A (150:8:1) gave the title compound 1.1 g), m.p. 133°–135°.

Intermediates 11 to 14 were prepared in a similar manner to Intermediate 10, i.e. by treating 2,3,4,5-tetrahydro-1H-pyrido[4,3-b]indol-1-one with sodium hydride followed by an appropriate alkylating agent. Isolation and purification of the products were as described for Intermediate 10 unless otherwise stated.

Intermediate 11

5-Ethyl-2,3,4,5-tetrahydro-1H-pyrido[4,3-b]indol-1-one 2,3,4,5-Tetrahydro-1H-pyrido[4,3-b]indol-1-one (931 mg) was treated with sodium hydride (60% dispersion in oil; 400 mg) and was then stirred with ethyl iodide (10% v/v solution in DMF; 4 ml) to give the title compound (758 mg), m.p. 203°–204.5°.

Intermediate 12

2,3,4,5-Tetrahydro-5-(1-methylethyl)-1H-pyrido[4,3-b]indol-1-one 2,3,4,5-Tetrahydro-1H-pyrido[4,3-b]indol-1-one (931 mg) was treated with sodium hydride (73% dispersion in oil; 328 mg) and was then stirred with 2-bromopropane (615 mg) at room temperature for 72 h. Purification by FCC eluting with System A (200:8:1) gave a foam (324 mg) which was further purified by recrystallisation from ethyl acetate: hexane (1:1) to give the title compound (249 mg), t.l.c. (System A, 100:8:1) Rf 0.58.

Intermediate 13

2,3,4,5-Tetrahydro-5-(phenylmethyl)-1H-pyrido[4,3-b]indol-1-one 2,3,4,5-Tetrahydro-1H-pyrido[4,3-b]indol-1-one (559 mg) was treated with sodium hydride (73% dispersion in oil; 197 mg) and was then stirred with benzyl bromide (513 mg) at room temperature for 30 min. Purification by FCC eluting with dichloromethan: ethanol (80:1) gave the title compound (347 mg), m.p. 209°–212°.

Intermediate 14

5-(Cyclopentylmethyl)-2,3,4,5-tetrahydro-1H-pyrido[4,3-b]indol-1-one 2,3,4,5-Tetrahydro-1H-pyrido[4,3-b]indol-1-one (950 mg) was treated with sodium hydride (60% dispersion in oil; 408 mg) and was then stirred with cyclopentahemethanol (methane sulphonate) (909 mg) at room temperature for 7 days. The solid (570 mg) obtained by FCC was further purified by slow evaporation form a solution in methanol to give the title compound, m.p. 179°–181°.

Intermediate 15

2,3,4,5-Tetrahydro-2-[[5-methyl-1-(triphenylmethyl)-1H-imidazol-4-yl]methyl]-1H-pyrido[4,3-b]indol-1-one A solution of triphenylmethyl chloride (3.36 g) in dry DMF (40 ml) was added dropwise to a stirred solution of 2,3,4,5-tetrahydro-2-](5-methyl-1H-imidazol-4-yl)methyl]-1H-pyrido[4,3-b]indol-1-one (2.8 g) in dry DMF (50 ml) containing triethylamine (1.52 g). When addition was complete the mixture was stirred overnight. The mixture was then poured into water (1000 ml) and the resulting suspension was extracted with ethyl acetate (3×300 ml). The combined organic extracts were washed with water (2×500 ml), dried and concentrated onto silica. FCC eluting with System A (100:8:1) gave the title compound (4.3 g), m.p. 235°–236°.

Intermediate 16

2,3,4,5-Tetrahydro-5-methyl-2-[[1-(triphenylmethyl)-1H-imidazol-4-yl]methyl]-1H-pyrido[4,3-b]indol-1-one A mixture of 2,3,4,5-tetrahydro-5-methyl-1H-pyrido[4,3-b]indol-1-one (0.3 g) and sodium hydride (80% dispersion in oil; 0.05 g) in dry DMF (5 ml) was stirred under nitrogen at 50° until hydrogen evolution ceased (ca. 0.5 h). The mixture was cooled to 40° and a solution of 4-(chloromethyl)-1-(triphenylmethyl)-1H-imidazole (0.53 g) in dry THF (3 ml) was added. The mixture was stirred at 40° to 23° over 2 h, poured into water (100 ml) and extracted with dichloromethane (3×100 ml). The dried organic phase was evaporated to give a semi-solid which was purified by FCC eluting with dichloromethane:ethyl acetate:triethylamine (50:50:1) to give a solid. This was slurried in hexane and filtered to give the title compound (0.37 g), m.p. 205°–210° (decomp.).

Intermediate 17

2,5-Dihydro-5-methyl-1H-pyrido[4,3, -b]indol-1-one

A mixture of 2,3,4,5-tetrahydro-5-methyl-1H-pyrido[4,3-b]indol-1-one (500 mg) and 10% palladium oxide on carbon catalyst (50% aqueous paste; 250 mg) was heated at 320° for 10 min. The cooled solid was triturated with ethanol (ca. 100 ml), filtered and the resulting filtrate was evaporated to give the title compound (470 mg), m.p. 242.5°.

Intermediate 18

2,5-Dihydro-5-methyl-2-[(5-methyl-1H-imidazol-4-yl)methyl]-1H-pyrido[4,3-b]indol-1-one maleate Sodium hydride (73% dispersion in oil; 80 mg) was added to a stirred suspension of 2,5-dihydro-5-methyl-1H-pyrido[4,3-b]indol-1-one (440 mg) in dry dimethoxyethane (25 ml) under nitrogen and the mixture was heated at 50° for 6 h. 4-(Chloromethyl)-5-methyl-1-(triphenylmethyl)-1H-imidazole (910 mg) was then added, and stirring was continued at 50° for 20 h. Water (4.5 ml) and acetic acid (4.5 ml) were added and the solution was heated at reflux for 5 h. The mixture was poured into 8% sodium bicarbonate solution (80 ml) and extracted with dichloromethan:ethanol (10:1; 3×40 ml). The combined, dried organic extracts were evaporated to give a solid (ca. 1.5 g) which was purified by FCC eluting with System A (100:10:1) to give the free base of the title compound as a solid (348 mg). A sample of this solid (100 mg) was dissolved in absolute ethanol (20 ml) and treated with a solution of maleic acid (40 mg) in absolute ethanol (1 ml). The solvent was removed in vacuo and the residue was triturated with dry ether (3×20 ml) to give a solid (115 mg) which as re-crystallised from methanol-ethyl acetate to give the title compound (40 mg), m.p., 166°–168°.

Intermediate 19

5,6-Dihydro-4-methoxy-1-[[5-methyl-1-(triphenylmethyl)-1H-imidazol-4-yl]methyl]-2(1H)-pyridinone Sodium hydride (80% dispersion in oil; 360 mg) was suspended in dry DME (50 ml) under nitrogen and 5,6-dihydro-4-methoxy-2(1H)-pyridinone (1.27 g) in dry DME (20 ml) was added slowly. The resulting suspension was stirred at 20° for 1 h. 4-(Chloromethyl)-5-methyl-1-(triphenylmethyl)-1H-imidazole (3.72 g) in dry DME (50 ml) was added, and after the initial reaction had subsided the mixture was heated to 50° for 4 h and then cooled. Methanol (5 ml) was added dropwise, and solvent was removed invacuo. 8% Aqueous sodium bicarbonate solution (300 ml) was added to the residue and the resulting solution was extracted with dichloromethane (2×300 ml), dried and evaporated in vacuo to leave an oil which was purified by FCC eluting with System A (200:8:1) to give the title compound (2.84 g), m.p. 181°–184°.

Intermediate 20

2,4-Dioxo-1-[(5-methyl-1H-imidazol-4-yl)methyl]-piperidine

To a solution of 5,6-dihydro-4-methoxy-1-[[5-methyl-1-(triphenylmethyl)-1H-imidazol-4yl]methyl]-2(1H)-pyridinone (500 mg) in THF (4 ml) was added hydrochloric acid (5M; 1 ml), and the mixture was stirred at 50° for 1 h. The solvent was removed in vacuo, triethylamine (1 ml) was added, and the mixture was again evaporated to dryness. FCC of the residue eluting with ethyl acetate:methanol:triethylamine (8:4:1) gave the title compound (139 mg), m.p. 100°-106° (decomp.).

Intermediate 21

5,6-Dihydro-1-](5-methyl-1H-imidazol-4-yl)methyl]-4-(2-methyl-2-phenylhydrazino)-2(1H)-pyridinone 2,4-Dioxo-1-[(5-methyl-1H-imidazol-4-yl)methyl]-piperidine (200 mg) was dissolved in ethanol (2 ml) and N-methylphenylhydrazine (26 mg) was added. The mixture was stirred for 1 h and the solvent was removed in vacuo. The residue was purified by FCC eluting with system A (75:8:1) to give the title compound (24 mg) as a solid, t.l.c. (System A, 75:8:1) Rf 0.27.

Intermediate 22

N,N,5-Trimethyl-4-[[(trimethylsilyl)oxy]methyl]-1H-imidazole-1-sulphonamide

A suspension of 4-(hydroxymethyl)-5-methylimidazole hydrochloride (14.9 g) in dry dichloromethane (500 ml) containing triethylamine (50 g) was treated with trimethylsilyl chloride (21.7 g) and the reaction mixture was stirred at room temperature overnight. Dimethylsulphamoyl chloride (14.3 g) was added and the reaction mixture was again stirred at room temperature overnight. The resulting suspension was filtered and the collected solid was washed with dichloromethane (100 ml). The filtrate was concentrated onto silica and purification by FCC eluting with hexane:ether (4:1) gave the title compound as an oil (7.2 g), t.l.c. (ether) Rf 0.5.

Intermediate 23

4-(Hydroxymethyl)-N,N5-trimethyl-1H-imidazole-1-sulphonamide

A solution of N,N,5-trimethyl-4-[[(trimethylsilyl)oxy]methyl]-1H-imidazole-1-sulphonamide (2.59 g) in dry THF (50 ml) was treated with a solution of tetrabutylammonium fluoride (1M solution in THF; 10 ml). and the THF was immediately removed in vacuo. The residue was partitioned between water (100 ml) and dichloromethane (100 ml) and the aqueous layer was extracted with dichloromethane (100 ml). The combined, dried organic fractions were concentrated to give the title compound (1.63 g) as a solid, m.p. 134°-136°.

Intermediate 24

4-(Chloromethyl)-N,N,5-trimethyl-1H-imidazole-1-sulphonamide

A suspension of 4-(hydroxymethyl)-N,N,5-trimethyl-1H-imidazole-1-sulphonamide (2.86 g) in dry dichloromethane (200 ml) containing DMF (0.5 ml) was treated dropwise with a solution of thionyl chloride (1.178 g) in dichloromethane (10 ml). The reaction mixture was cooled in ice during the addition and blanketed with nitrogen. When addition was complete (ca. 5 min), stirring was continued at 0° for a further 30 min. Water (200 ml) was then added and the organic phase was separated, washed with 8% sodium bicarbonate (100 ml), dried and concentrated to give the title compound (2.3 g) as a solid, m.p. 115°-118°.

Intermediate 25

5,6-Dihydro-4-[(2-iodophenyl)methylamino]-2(1H)-pyridinone

A mixture of 2-iodo-(N-methyl)aniline (1.17 g) and 2,4-dioxopiperidine (565 mg) was heated under a stream of nitrogen for 7 h at 110°-120°. After cooling the reaction mixture was dissolved in methanol and the solution was adsorbed onto FCC silica. Purification by FCC eluting with System A (150:8:1) gave the title compound (1.03 g), m.p. 163°-164°.

Intermediate 26

N,N5-Trimethyl-4-[1,2,3,6-tetrahydro-4-[(2-iodophenyl)-methylamino]-6-oxo-1-pyridinyl]methyl-1H-imidazole-1-sulphonamide A suspension of 5,6-dihydro-4-[(2-iodophenyl)methylamino]-2(1H)-pyridinone (984 mg) in dry DME (50 ml) was treated with sodium hydride (60% dispersion in oil; 140 mg), and the mixture was stirred under nitrogen for 6 h. 4-(Chloromethyl)-N,N,5-trimethyl-1H-imidazole-1-sulphonamide (832 mg) was then added and the resulting mixture was stirred at 60° overnight. After cooling the reaction mixture was poured into water (100 ml), and the mixture was extracted with ethyl acetate (2×50 ml). The combined, dried organic extracts were concentrated, and the resultant solid was purified by FCC eluting with System A (150:8:1) to give the title compound (712 mg), t.l.c. (System A, 150:8:1) Rf 0.41.

Intermediate 27

N,N,5-Trimethyl-4-[(2,3,4,5-tetrahydro-5-methyl-1-oxo-1H-pyrido[4,3-b]indol-2-yl)methyl]-1H-imidazole-1-sulphonamide A solution of dimethylsulphamoyl chloride (0.107 ml) in dry dichloromethane was added to a stirred solution of 2,3,4,5-tetrahydro-5-methyl-2-[(5-methyl-1H-imidazol-4-yl)methyl]-1H-pyrido[4,3-b]indol-1-one (0.294 g) and triethylamine (0.2 ml) in dry dichloromethane (30 ml) under nitrogen, and the mixture was heated at reflux for ca. 24 h. After cooling the solution was concentrated onto FCC silica and purified by FCC eluting with System A (150:8:1) to give an oil. This oil was triturated with ether to give a solid which was further purified by slow evaporation from a solution in ethyl acetate to give the title compound (122 mg), m.p. 194°-196°, t.l.c. (System A, 100:8:1) Rf 0.43.

Intermediate 28

Phenylmethyl 5-methyl-4-[(2,3,4,5-tetrahydro-5-methyl-1-oxo-1H-pyrido[4,3-b]indol-2yl)methyl]-1H-imidazole-1-carboxylate A solution of benzyl chloroformate (0.28 ml) in dichloromethane (10 ml) was added to a stirred solution of 2,3,4,5-tetrahydro-5-methyl-2-[(5-methyl-1H-imidazol-4-yl)methyl]-1H-pyrido[4,3-b]indol-1one (294 mg) and triethylamine (0.4 ml) in dichloromethane (30 ml) at 20° under nitrogen, and the mixture was stirred overnight. It was then concentrated onto FCC silica and purified by FCC eluting with System A (200:8:1) to give the title compound (62 mg), t.l.c. (System A, 100:8:1) Rf 0.50.

Intermediate 29

2,3,4,5-Tetrahydro-2-[[1-(methoxymethyl)-5-methyl-1H-imidazol-4-yl]-methyl]-5-methyl-1H-pyrido[4,3-b]indol-1-one and
2,3,4,5-Tetrahydro-2-[[1-(methoxymethyl)-4-methyl-1H-imidazol-5yl]methyl]-5-methyl-1H-pyrido[4,3-b]indol-1-one A solution of chloromethyl methyl ether (0.26 ml) in dichloromethane (10 ml) was added to a stirred solution of 2,3,4,5-tetrahydro-5-methyl-2[(5-methyl-1H-imidazol-4-yl)methyl]-1H-pyrido[4,3-b]indol-1-one (500 mg) and triethylamine (0.49 ml) in dichloromethane (50 ml) at 20° under nitrogen, and the solution was stirred for 4 days. It was then partitioned between dichlormethane (50 ml) and sodium bicarbonate solution (2×50 ml). The organic extract was dried, concentrated onto FCC silica, and then purified by FCC elution with System A (100:8:1) to give the title compounds (139 mg). A portion of the title compound (64 mg) was taken up in hot ethyl acetate and purified by slow evaporation from ethyl acetate to give the title compounds.

Analysis Found: C67.3; H,6.9; N,16.5; $C_{19}H_{22}N_4O_2$ requires C,67.4; H,6.6; N,16.6%.

Intermediate 30

2,3,4,5-Tetrahydro-5-methyl-2-[(4-methyloxazol-5-yl)methyl]-1H-pyrido[4,3-b]-indol-1-one Sodium hydride (60% dispersion in oil; 600 mg) was added to a stirred suspension of 2,3,4,5-tetrahydro-5-methyl-1H-pyrido[4,3-b]indol-1-one (1.5 g) in dry DME (150 ml) and then the mixture was stirred at 60° for 5 h under nitrogen. 5-Chloromethyl-4-methyloxazole (1.2 g) was added and the mixture was stirred overnight. A further quantity of sodium hydride (60% dispersion in oil; 600 mg) was added and the mixture was stirred at 60° for 4 h, then cautiously treated with water (100 ml). The mixture was extracted with dichloromethane containing methanol (ca. 1%) (3×100 ml) and the combined extracts were evaporated. The residue was purified by FCC eluting with System A (100:8:1) to give the title compound (300 mg) as a solid, t.l.c. (System A, 100:8:1) Rf 0.4.

Intermediate 31

N-[(1-Methyl-1H-indol-2-yl)ethyl]trifluoroacetamide

A solution of 2-(1-methyl-1H-indol-2-yl)ethanamine (3.48 g) in dry dichloromethane (50 ml) containing triethylamine (2.53 g) was cooled in an ice bath, and trifluoroacetic anhydride (5.25 g) was added dropwise over 15 min. The mixture was then allowed to warm to room temperature and stirred for an additional 3 h. After this time the reaction mixture was poured into water (100 ml), the organic phase was separated, and the aqueous phase was washed with dichloromethane (2×50 ml). The combined, dried organic extracts were concentrated onto FCC silica and purification by FCC eluting with ether gave the title compound (4.2 g) as a solid. A sample of this compound was further purified by slow evaporation from a solution in dichloromethane, m.p. 124°–126°.

Intermediate 32

N,N,5-Trimethyl-4-[[(1-methyl-1H-indol-2-yl)-N-trifluoroacetylamino]-ethyl]imidazole-1-sulphonamide A solution of N-[(1-methyl-1H-indol-2-yl)ethyl]trifluoroacetamide (2.7 g) in dry DMF (100 ml) was treated with sodium hydride (60% dispersion in oil; 480 mg), and the mixture was stirred at room temperature for 30 min. 4-(Chloromethyl)-N,N,5-trimethyl-1H-imidazole-1-sulphonamide (2.37 g) was then added and the mixture was stirred at room temperature overnight. After this time the reaction mixture was poured into water (500 ml) and the resulting suspension was extracted with ethyl acetate (2×100 ml). The combined organic extracts were washed with water (5×250 ml), dried and adsorbed onto FCC silica. Purification by FCC eluting with System A (150:8:1) gave the title compound (1.9 g), m.p. 156°–158°.

Intermediate 33

4-[[[(1-Methyl-1H-indol-2-yl)ethyl]amino]methyl]-N,N,5-trimethyl-1H-imidazole-1-sulphonamide A mixture of N,N,5-trimethyl-4[[(1-methyl-1H-indol-2-yl)-N-trifluoro-acetylamino]ethyl]imidazole-1-sulphonamide (260 mg), methanol (10 ml) and saturated aqueous potassium carbonate solution (5 ml) was heated to 60° for 1.5 h. After cooling the mixture was poured into water (50 ml) and the mixture was extracted with ethyl acetate (2×50 ml). The combined, dried organic extracts were concentrated onto FCC silica and purified by FCC eluting with System A (150:8:1) to give the title compound (143 mg) as an oil, t.l.c. (System A, 100:8:1) Rf 0.51.

Intermediate 34

4-[[[(3-Iodo-1-methyl-1H-indol-2-yl)ethyl]trifluoroacetylamino]-methyl]-N,N,5-trimethyl-1H-imidazole-1-sulphonamide A solution of 4-[[[(1-methyl-1H-indol-2-yl)ethyl]amino]methyl]-N,N,5-trimethyl-1H-imidazole-1-sulphonamide (471 mg) in methanol (25 ml) containing potassium carbonate (138 mg) was treated with a solution of iodine (254 mg) and potassium iodide (166 mg) in water (30 ml) over 30 min. When addition was complete the reaction mixture was stirred for a further 2 h. After this time additional methanol was removed in vacuo and the resulting suspension was extracted with ethyl acetate (3×25 ml). The combined organic extracts were concentrated onto FCC silica and purified by FCC eluting with System A (150:8:1) to give the title compound (367 mg), m.p. 141°–143°.

Intermediate 35

4-[[[(3-Iodo-1-methyl-1H-indol-2-yl)ethyl]amino]methyl]-N,N,5-trimethyl-1H-imidazole-1-sulphonamide 4-[[[(3-Iodo-1-methyl-1H-indol-2-yl)ethyl]trifluoroacetylamino]-methyl]-N,N,5-trimethyl-1H-imidazole-1-sulphonamide (199 mg) was deprotected according to the method described in Intermediate 33 to give the title compound (50 mg) as an oil, t.l.c. (System A, 150:8:1) Rf 0.51.

EXAMPLE 1

2,3,4,5-Tetrahydro-5-methyl-2-[(5-methyl-1H-imidazol-4-yl)methyl]-1H-pyrido[4,3-b]indol-1-one maleate A mixture of 2,3,4,5-tetrahydro-5-methyl-1H-pyrido[4,3-b]indol-1-one (0.6 g) and ca. 78% sodium hydride dispersion in mineral oil (0.109 g) in dry DMF (15 ml) was stirred under nitrogen at 50° until hydrogen evolution ceased (ca. 1.5 h). The mixture was cooled to 40° and a solution of 4-(chloromethyl)-5-methyl-1-(triphenylmethyl)-1H-imidazole (1.12 g) in dry THF (15 ml) was added. The reaction was then stirred at 40° for 3 h, at 20° for 16 h and a further portion of 4-(chloromethyl)-5-methyl-1-(triphenylmethyl)-1H-imidazole (1.12 g) in dry THF (15 ml) was added. The resulting mixture was heated at 40° for 3 h, quenched with water (20 ml) and acetic acid (20 ml), and heated at 100° for 2 h. The mixture was then concentrated in vacuo to ca. 60 ml, diluted with 1M hydrochloric acid (40 ml) and washed with ethyl acetate (3×50 ml). The organic phase was discarded and the acidic aqueous phase was basified (pH9) with potassium carbonate and extracted with ethyl acetate: ethanol (20:1, 3×100 ml). The extracts were combined, dried and evaporated to give a brown gum (ca. 1 g). This gum was adsorbed onto silica and purified by FCC eluting with System A (100:8:1) to give a pale brown solid (0.8 g) m.p. 238°–240° (decomp). This solid was dissolved in a mixture of hot ethanol and methanol (1:1; 100 ml) and treated with an ethanolic solution of maleic acid (318 g). The resulting solution was concentrated to ca. 20 ml and diluted with dry diethyl ether (ca. 8 ml) to precipitate the title compound (0.75 g) as an off-white solid, m.p. 160°–162°.

Analysis Found: C,61.6; H,5.5; N,13.6; $C_{17}H_{18}N_4O.C_4H_4O_4$ requires C,61.5; H,5.4; N,13.8%.

EXAMPLE 2

3,4,5,6-Tetrahydro-6-methyl-2-[(5-methyl-1H-imidazol-4-yl)methyl]-azepino[4,3-b]indol-1(2H)-one maleate 3,4,5,6-Tetrahydro-6-methylazepino[4,3-b]indol-1-(2H)-one (0.64 g) was treated with sodium hydride (ca. 75–80% dispersion in oil; 0.108 g) and was then stirred with 4-(chloromethyl)-5-methyl-1-(triphenylmethyl)-1H-imidazole as described in Example 1. The reaction mixture was then poured into water (300 ml) and extracted with dichloromethane (4×250 ml). The combined, dried organic extracts were evaporated to give a semi-solid (ca. 1.8 g) which was purified by FCC eluting with System A (200:8:1) to give a gum (0.7 g). The gum (0.7 g) was dissolved in a mixture of acetic acid, THF and water (1:1:1; ca. 70 ml) and heated on a steam bath for 1 h. Work-up as described in Example 1 gave a gum (0.22 g) which was purified by FCC eluting with System A (200:8:1) to give a solid (0.11 g). Maleate formation gave a gum which was dried in vacuo to give a foam which was triturated with a mixture of ether and ethanol (50:1; ca. 25 ml) to give the title compound (0.145 g) as a solid, m.p. 132°–133°.

1H-N.m.r. indicated 0.39 mol of ethanol present. Water Analysis Found 0.583% w/w≡0.14 mol H₂O. Analysis Found: C,61.4; H,5.7; N,12.6; $C_{18}H_{20}N_4O.C_4H_4O_4.0.39EtOH$. 0.14 H₂O requires C,61.4; H,6.0; N,12.6%.

EXAMPLE 3

2,3,4,5-Tetrahydro-2[(5-methyl-1H-imidazol-4-yl)methyl]-5-[(phenylmethoxy)methyl]-1H-pyrido[4,3-b]indol-1-one maleate A suspension of 2,3,4,5-tetrahydro-5-[(phenylmethoxy)methyl]-1H-pyrido[4,3-b]indol-1-one (920 mg) in dry DME (75 ml) was treated with sodium hydride (60% dispersion in oil; 180 mg) under nitrogen and the reaction mixture was stirred at 60° for 6 h.

4-(Chloromethyl)-5-methyl-1-(triphenylmethyl)-1H-imidazole (1.11 g) was then added and the mixture was stirred at 60° overnight. Acetic acid (10 ml), water (10 ml) and THF (10 ml) were then added and the resulting solution was heated at reflux for 6 h. After cooling, 2N sodium hydroxide (100 ml) was added and the resulting suspension was extracted with dichloromethane (3×100 ml). The combined, dried organic extracts were adsorbed onto FCC silica, and FCC eluting with System A (150:8:1) gave the free base of the title compound (1.08 g) as a foam. A small amount of this compound (200 mg) was dissolved in methanol (30 ml) and the resulting solution was treated with maleic acid (58 mg). The solution was heated for 10 min., cooled, and dry ether was added to precipitate the title compound (170 mg), m.p. 165°–168°.

Water Analysis Found 0.22% w/w≡0.06 mol H₂O. Analysis Found: C,64.5; H,5.6; N,10.7; $C_{24}H_{24}N_4O.C_4H_4O_4$. 0.06 H₂O requires C,65.0; H,5.5; N,10.8%.

Examples 4 to 7 were prepared in a similar manner to Example 3.

EXAMPLE 4

5-Ethyl-2,3,4,5-tetrahydro-2-[(5-methyl-1H-imidazol-4-yl)methyl]-1H-pyrido[4,3-b]indol-1-one maleate 5-Ethyl-2,3,4,5-tetrahydro-1H-pyrido[4,3-b]indol-1-one (500 mg) was treated with sodium hydride (60% dispersion in oil; 138 mg) and was then stirred with 4-(chloromethyl)-5-methyl-1-(triphenylmethyl)-1H-imidazole (927.5 mg) to give the free base of the title compound (320 mg) as a solid. Maleate formation gave the title compound (380 mg), m.p. 175.5°–177°.

Analysis Found: C,62.1; H,5.7; N,13.0; $C_{18}H_{20}N_4O.C_4H_4O_4$ requires C,62.2; H,5.7; N,13.2%.

EXAMPLE 5

2,3,4,5-Tetrahydro-5-(1-methylethyl)-2-[(5-methyl-1H-imidazol-4-yl)methyl]-1H-pyrido[4,3-b]indol-1-one maleate 2,3,4,5-Tetrahydro-5-(1-methylethyl)-1H-pyrido[4,3-b]indol-1-one (228 mg) was treated with sodium hydride (60% dispersion in oil; 60 mg) and was then stirred with 4-(chloromethyl)-5-methyl-1-(triphenylmethyl)-1H-imidazole (371 mg) to give the free base of the title compound (180 mg) as a solid. Maleate formation gave the title compound (172 mg), m.p. 203°–205°.

Analysis Found: C,62.6; H,6.0; N,12.6; $C_{19}H_{22}N_4O.C_4H_4O_4$ requires C,63.0; H,6.0; N,12.8%.

EXAMPLE 6

2,3,4,5-Tetrahydro-5-(phenylmethyl)-2-[(5-methyl-1H-imidazol-4-yl)-methyl]-1H-pyrido[4,3-b]indol-1-one maleate monohydrate 2,3,4,5-Tetrahydro-5-(phenylmethyl)-1H-pyrido[4,3-b]indol-1-one (960 mg) was treated with sodium hydride (73% dispersion in oil; 132 mg) and was then stirred with 4-(chloromethyl)-5-methyl-1-(triphenylmethyl)-1H-imidazole (1.3 g). The free base of the title compound (571 mg) was obtained as a solid by FCC eluting with System A (175:8:1). Maleate formation gave the title compound (420 mg), m.p. 198°–200°, t.l.c. (System A, 100:8:1) Rf 0.3.

EXAMPLE 7

5-(Cyclopentylmethyl)-2,3,4,5-tetrahydro-2-[(5-methyl-1H-imidazol-4-yl)methyl]-1H-pyrido[4,3-b]indol-1-one maleate 5-(Cyclopentylmethyl)-2,3,4,5-tetrahydro-1H-pyrido[4,3-b]indol-1-one (200 mg) was treated with sodium hydride (60% dispersion in oil; 60 mg) and was then stirred with 4-(chloromethyl)-5-methyl-1-(triphenylmethyl)-1H-imidazole (280 mg). The free base of the title compound was obtained as a solid (96 mg) by FCC eluting with System A (200:8:1). Maleate formation gave the title compound (60 mg), m.p. 81°–83°, t.l.c. (System A, 100:8:1) Rf 0.20.

EXAMPLE 8

2,3,4,5-Tetrahydro-5-methyl-2-[(5-propyl-1H-imidazol-4-yl)methyl]-1H-pyrido[4,3-b]indol-1-one maleate Sodium hydride (60% dispersion in oil; 25 mg) was added to a stirred suspension of 2,3,4,5-tetrahydro-5-methyl-1H-pyrido[4,3-b]indol-1-one (124 mg) in dry DME (5 ml) under nitrogen. The mixture was heated at 50° for 7 h and then treated with a solution of 4-(chloromethyl)-N,N-dimethyl-5-propyl-1H-imidazole-1-sulphonamide (165 mg) in dry DME (3 ml) and stirring was continued at 50° for 20 h. 2N Hydrochloric acid (5 ml) was added and the solution was heated at reflux for 6 h. The solution was poured into 8% sodium bicarbonate solution (50 ml) and extracted with dichloromethane (3×25 ml). The combined, dried organic extracts were evaporated to give a solid (200 mg) which was purified by FCC eluting with System A (200:10:1) to give the free base of the title compound (58 mg) as a solid. This was dissolved in warm absolute ethanol (5 ml) and treated with a solution of maleic acid (21 mg) in ethanol (0.5 ml). The solvent was removed in vacuo and the residue was crystallised from ethanol:ether to give the title compound (58 mg), m.p. 137°–138°.

Analysis Found: C,62.7; H,5.9; N,12.4; $C_{19}H_{22}N_4O.C_4H_4O_4$ requires C,63.0; H,6.0; N,12.8%.

EXAMPLE 9

2,3,4,5-Tetrahydro-N,N-dimethyl-2-[(5-methyl-1H-imidazol-4-yl)methyl]-1-oxo-5H-pyrido[4,3-b]indole-5-carboxamide maleate A solution of 2,3,4,5-tetrahydro-2-[[5-methyl-1-(triphenylmethyl)-1H-imidazol-4-yl]methyl]-1H-pyrido[4,3-b]indol-1-one (261 mg) in dry DMF (25 ml) was treated with sodium hydride (60% dispersion in oil; 30 mg) and the mixture was stirred at room temperature under nitrogen for 15 min. N,N-Dimethylcarbamoyl chloride (1M solution in DMF; 1 ml) was then added and the solution was stirred at room temperature for an additional 15 min. Water (1 ml) was cautiously added, and the reaction mixture was then poured into water (100 ml). The resulting mixture was extracted with ethyl acetate (2×50 ml) and the combined organic extracts were washed with water (2×100 ml) and concentrated to give an oil. The oil was dissolved in a mixture of water (10 ml), glacial acetic acid (10 ml) and THF (10 ml) and the solution was heated at reflux for 1.5 h. After cooling the solution was basified by addition of 2N sodium hydroxide (100 ml), and the resulting mixture was extracted with ethyl acetate (2×75 ml). The combined, dried organic extracts were adsorbed onto FCC silica and the free base of the title compound (110 mg) was obtained by FCC eluting with System A (100:8:1) as a solid. This was dissolved in dry methanol (10 ml) and heated with maleic acid (36 mg) on a steam bath for 5 min. On cooling, dry ether (3 ml) was added to precipitate the title compound (105 mg), m.p. 161°–163°.

Water Analysis Found 1.85% w/w=0.49 mol $H_2O$. Analysis Found: C,5.78; H,5.4; N,14.3; $C_{19}H_{21}N_5O_2.C_4H_4O_4$. 0.49 $H_2O$ requires C,68.0; H,5.5; N,14.7%.

Examples 10, 11 and 12 were prepared in a similar manner to Example 9 unless otherwise stated.

EXAMPLE 10

2,3,4,5-Tetrahydro-2-[(5-methyl-1H-imidazol-4-yl)methyl]-5-(methylsulphonly)-1H-pyrido[4,3-b]indol-1-one maleate 2,3,4,5-Tetrahydro-2-[[5-methyl-1-(triphenylmethyl)-1H-imidazol-4-yl]methyl]-1H-pyrido[4,3-b]indol-1-one (261 mg) was treated with sodium hydride (60% dispersion in oil; 30 mg) and was then stirred with methanesulphonyl chloride (1M solution in dry DMF; 1 ml) for 45 min. Deprotection, work-up and purification gave the free base of the title compound (60 mg) as a solid. Maleate formation gave the title compound (57 mg), m.p. 152°–155°.

Analysis Found: C,53.2; H,4.7; N,11.7; $C_{17}H_{18}N_4O_3S.C_4H_4O_4$ requires C,53.2; H,4.7; N,11.8%.

EXAMPLE 11

2,3,4,5-Tetrahydro-2-[(5-methyl-1H-imidazol-4-yl)methyl]-5-(2-propynyl)-1H-pyrido[4,3-b]indol-1-one maleate A suspension of 2,3,4,5-tetrahydro-2-[[5-methyl-1-(triphenylmethyl)-1H-imidazol-4-yl]methyl]-1H-pyrido[4,3-b]indol-1-one (522 mg) and potassium carbonate (276 mg) in dry acetone (75 ml) was treated with propargyl bromide (1M solution in acetone; 2 ml) and the mixture was heated at reflux overnight. After cooling, excess acetone was removed in vacuo to give an oil which was partitioned between water (100 ml) and ethyl acetate (100 ml). The aqueous phase was washed with ethyl acetate (50 ml) and the combined organic extracts were concentrated in vacuo. Deprotection, work-up and purification gave the free base of the title compound (100 mg) as a solid. Maleate formation gave the title compound (89 mg), m.p. 202°–205°, t.l.c. (System A, 100:8:1) Rf 0.29.

EXAMPLE 12

2,3,4,5-Tetrahydro-2-[(5-methyl-1H-imidazol-4-yl)methyl]-5-(2-propenyl)-1H-pyrido[4,3-b]indol-1-one maleate 2,3,4,5-Tetrahydro-2-[[5-methyl-1-(triphenylmethyl)-1H-imidazol-4-yl]methyl]-1H-pyrido[4,3-b]indol-1-one (1.0 g) was treated with sodium hydride (60% dispersion in oil; 114 mg) and was then stirred with allyl bromide (460 mg) for 1 h. Deprotection, work-up and purification gave the free base of the title compound (380 mg) as a solid. Maleate formation gave the title compound (160 mg), t.l.c. (System A, 100:8:1) Rf 0.3.

Analysis Found: C,63.2; H,5.5; N,12.5; $C_{19}H_{20}N_4O.C_4H_4O_4$ requires C,63.3; H,5.5; N,12.8%.

EXAMPLE 13

5-Cyclopentyl-2,3,4,5-tetrahydro-2[(5-methyl-1H-imidazol-4-yl)methyl]-1H-pyrido[4,3-b]indol-1-one maleate A solution of 2,3,4,5-tetrahydro-2-[[5-methyl-1-(triphenylmethyl)-1H-imidazol-4-yl]methyl]-1H-pyrido[4,3-b]indol-1-one (523 mg) in dry DMF (30 ml) was treated with sodium hydride (60% dispersion in oil; 46 mg) and stirred for 15 min. at 21° under nitrogen. Cyclopentyl bromide (298 mg) was then added dropwise, and the mixture was stirred for 1 h and then heated at reflux for 4 h. The solution was left at 21° for 2 days, and then treated with a mixture of acetic acid (7 ml), water (7 ml) and THF (8 ml). The resulting solution was heated at reflux for 4 h, then basified with 2N sodium hydroxide and extracted with dichloromethane (3×25 ml). The combined extracts were washed with water (2×50 ml), concentrated in vacuo and purified by FCC eluting with System A (100:8:1) to give the free base of the title compound (42 mg) as a solid. Maleate formation gave the title compound (38 mg), m.p. 180° (decomp.), t.l.c. (System A, 100:8:1) Rf 0.3.

EXAMPLE 14

2,3,4,5-Tetrahydro-2-[(5-methyl-1H-imidazol-4-yl)methyl]-5-propyl-1H-pyrido[4,3-b]indol-1-one maleate A solution of 2,3,4,5-tetrahydro-2-[(5-methyl-1H-imidazol-4-yl)methyl]-5-(2-propyl)-1H-pyrido[4,3-b]indol-1-one (248 mg) in a mixture of ethanol (20 ml) and 2N hydrochloric acid (0.5 ml) was hydrogenated at room temperature and atmospheric pressure over a pre-reduced 10% palladium oxide on carbon catalyst (50% aqueous paste; 50 mg). The mixture was filtered and evaporated in vacuo. The residue was basified with 2N sodium hydroxide (10 ml) and extracted with dichloromethane (3×20 ml). The combined organic extracts were washed with water (30 ml) and evaporated to give the free base of the title compound (258 mg) as a solid. Maleate formation gave the title compound 345 mg), t.l.c. (System A, 100:8:1) Rf 0.4.

Water Analysis Found 1.13% w/w≡0.28 mol $H_2O$.
Analysis Found: C,62.1; H,5.9; N,12.5; $C_{19}H_{22}N_4O.C_4H_4O_4$ 0.28 $H_2O$ requires C,62.2; H,6.0; N,12.6%.

EXAMPLE 15

2,3,4,5-Tetrahydro-2-[(5-methyl-1H-imidazol-4-yl)methyl]-1H-pyrido-[4,3-b]indol-1-one maleate A suspension of 2,3,4,5-tetrahydro-2-[(5-methyl-1H-imidazol-4-yl)-methyl]-5-[phenyl(methoxymethyl)]-1H-pyrido[4,3-b]indol-1-one (400 mg) in ethanol (20 ml) and glacial acetic acid (5 ml) was hydrogenated overnight at room temperature and atmospheric pressure over a pre-reduced 10% palladium oxide on carbon catalyst (50% aqueous paste; 100 mg). The reaction mixture was filtered and the residue was washed with ethanol (100 ml). The filtrate was concentrated in vacuo to give an oil, to which was added 2N sodium hydroxide (50 ml). The resulting suspension was extracted with dichloromethane (2×50 ml) and the combined, dried organic extracts were evaporated to give a solid. This was purified by FCC eluting with System A (75:8:1) to give the free base of the title compound as a solid (240 mg) which was then dissolved in dry methanol (50 ml). Maleate formation gave the title compound (261 mg), t.l.c. (System A, 75:8:1) Rf 0.2

Analysis Found: C,60.3; H,5.2; N,13.8; $C_{16}H_{16}N_4O.C_4H_4O_4$ requires C,60.6; H,5.1; N,14.1%.

EXAMPLE 16

2,3,4,5-Tetrahydro-5-methyl-2-[(I,5-dimethyl-1H-imidazol-4-yl)methyl]-1H-pyrido[4,3-b]indol-1-one maleate Sodium hydride (73% dispersion in oil; 40 mg) was added to a stirred suspension of 2,3,4,5-tetrahydro-5-methyl-2-[(5-methyl-1H-imidazol-4-yl)methyl]-1H-pyrido[4,3-b]indol-1-one (300 mg) in dry DMF (3 ml) under nitrogen. After 30 min. the suspension was cooled to 0° and iodomethane (0.076 ml) was added dropwise. The mixture was allowed to reach room temperature, stirred for 1.5 h, then poured into water (30 ml) and extracted with dichloromethane (3×15 ml). The combined, dried organic extracts were evaporated to give an oil (ca. 545 mg) which was purified by FCC eluting with System A (200:8:1) to give a solid (95 mg). A portion of this material (90 mg) was dissolved in absolute ethanol (3 ml) and treated with a solution of maleic acid (35 mg) in absolute ethanol (1 ml). The solvent was removed in vacuo and the residue was triturated with dry ether (3×5 ml) to give the title compound (122 mg), m.p. 178°–180°.

Analysis Found: C,62.1; H,5.7; N,13.1; $C_{18}H_{20}N_4O.C_4H_4O_4$ requires C,62.3; H,5.7; N,13.2%.

EXAMPLE 17

2,3,4,5-Tetrahydro-2-[(1H-imidazol-4-yl)methyl]-5-methyl-1H-pyrido[4,3-b]indol-1-one dimaleate A solution of 2,3,4,5-tetrahydro-5-methyl-2-[[(1-(triphenylmethyl)-1H-imidazol-4-yl]methyl]-1H-pyrido[4,3-b]indol-1-one (0.22 g) in a mixture of acetic acid, THF and water (1:1:1; 10 ml) was heated on a steam bath for 30 min. The suspension so obtained was diluted with 1M hydrochloric acid (20 ml) and washed with ethyl acetate (3×20 ml). The acidic aqueous phase was basified with solid sodium carbonate and extracted with dichloromethane:methanol (9:1; 3×20 ml). The combined, dried organic extracts were evaporated to give a foam which was dissolved in methanol (5 ml) and treated with a solution of maleic acid (0.15 g) in methanol (5 ml). The clear solution was evaporated to give a gum which on trituration with ether afforded the title compound (0.17 g) as a solid, m.p. 117°–118°.

Analysis Found: C,56.1; H,4.3; N,10.5; $C_{16}H_{16}N_4O.2C_4H_4O_4$ requires C,56.2; H,4.7; N,10.9%.

EXAMPLE 18

2,3,4,5-Tetrahydro-5-methyl-2-[(5-methyl-1H-imidazol-4-yl)methyl]-1H-pyrido[4,3-b]indol-1-one hydrochloride 2,3,4,5-Tetrahydro-5-methyl-2-[(5-methyl-1H-imidazol-4-yl)methyl]-1H-pyrido[4,3-b]indol-1-one (1.00 g) was suspended in ethanol (40 ml) and concentrated hydrochloric acid (1.00 ml) was added. The mixture was warmed to 40° and charcoal (0.25 g) was added. The resulting suspension was stirred and warmed for 5 min. and then filtered. The filtrate was evaporated in vacuo to ca. 20 ml and was allowed to cool to 20°. Ether (40 ml) was added with stirring over 5 min., and the mixture was stored at 4° overnight. The resulting precipitate was filtered off, washed with ether (2×10 ml), dried in vacuo at room temperature for 2 h and then at 70° for 7 h to give the title compound (0.95 g), m.p. 288°–291°.

Analysis Found: C,61.4; H,5.8; N,16.7; Cl, 10.7; $C_{17}H_{18}N_4O \cdot HCl$ requires C,61.7; H,5.8; N,16.9; Cl, 10.7%.

EXAMPLE 19

2,3,4,5-Tetrahydro-5-methyl-2-[(5-methyl-1H-imidazol-4-yl)methyl]-1H-pyrido[4,3-b]indol-1-one sulphate 2,3,4,5-Tetrahydro-5-methyl-2-[(5-methyl-1H-imidazol-4-yl)methyl]-1H-pyrido[4,3-b]indol-1-one (0.81 g) was suspended in absolute ethanol (6 ml) and was warmed at 50° with concentrated sulphuric acid (0.15 ml). More ethanol (4 ml) was added and the mixture was stirred with charcoal (0.1 g). The suspension was then filtered and the collected solid was washed with ethanol (ca. 3 ml). The resulting filtrate was stirred for ca. 1 h at room temperature, tert-butyl methyl ether (10 ml) was added slowly and the mixture was stirred for 20 min. The precipitate was filtered off, washed with ethanol:tert-butyl methyl ether (1:1;6 ml), then with tert-butyl methyl ether (6 ml), and dried in vacuo at 40° for 4 days to give the title compound (0.4 g), m.p. 205°–209°.

Analysis Found: C,49.5; H,5.6; N, 13.5; S,8.4; $C_{17}H_{18}N_4O \cdot 1.1H_2SO_4$ requires C,49.9; H,5.4; N, 13.3; S, 8.4%.

EXAMPLE 20

2,3,4,5-Tetrahydro-5-methyl-2-[(5-methyl-1H-imidazol-4-yl)methyl]-1H-pyrido[4,3-b]indol-1-one A suspension of 2,3,4,5-tetrahydro-5-methyl-1H-pyrido[4,3-b]indol-1-one (400 mg) in dry DME (50 ml) was treated with sodium hydride (60% dispersion in oil; 100 mg), and the mixture was stirred at 60° under nitrogen for 6 h. 4-(Chloromethyl)-5-methyl-1-(triphenylmethyl)-1H-imidazole (474 mg) was added and the reaction mixture was stirred at 60° under nitrogen overnight. 2N Hydrochloric acid (10 ml) and water (10 ml) were then added, and the mixture was heated at reflux for 6 h. After cooling, the mixture was basified with 2N sodium hydroxide and the resulting mixture was extracted with ethyl acetate (2×50 ml). The combined, dried organic extracts were concentrated onto FCC silica and purified by FCC eluting with System A (150:8:1) to give the title compound (352 mg) as a solid, t.l.c. (System A, 100:8:1) Rf 0.28. $^1$H-N.m.r.: δ2.2 (3H,s), 3.04 (2H,t), 3.62 (2H,t), 3.72 (3H,s), 4.53 (2H,s), 7.1–7.28 (2H,m), 7.43 (1H,s), 7.47–7.55 (1H,dd), 7.94–8.03 (1H,dd).

EXAMPLE 21

2,3,4,5-Tetrahydro-5-methyl-2-[(5-methyl-1H-imidazol-4-yl)methyl]-1H-pyrido[4,3-b]indol-1-one A mixture of 2,5-dihydro-5-methyl-2-[[(5-methyl-1H-imidazol-4-yl)-methyl]-1H-pyrido[4,3-b]indol-1-one (50 mg) and 10% palladium oxide on carbon catalyst (50% aqueous paste; 25 mg) in absolute ethanol (10 ml) was heated at 80° in a hydrogen atmosphere at 80 p.s.i. for 24 h. The suspension was filtered and the filtrate was evaporated to give an oil (49 mg) which was purified by short path column chromatography on silica gel (Merck 7739) eluting with System A (150:10:1) to give the title compound (8 mg) as a solid, t.l.c. (System A, 150:10:1) Rf 0.36. The $^1$H-n.m.r. data obtained for this material were consistent with those obtained for the product of Example 20.

EXAMPLE 22

2,3,4,5-Tetrahydro-5-methyl-2-[(5-methyl-1H-imidazol-4-yl)methyl]-1H-pyrido[4,3-b]indol-1-one A solution of 2,3,4,5-tetrahydro-2[[5-methyl-1-(triphenylmethyl)-1H-imidazol-4-yl]methyl]-1H-pyrido[4,3-b]indol-1-one (261 mg) in dry DMF (25 ml) was treated with sodium hydride (60% dispersion in oil; 30 mg) and the mixture was stirred at room temperature under nitrogen for 15 min. Iodomethane (0.5M solution in DMF; 2 ml) was then added and stirring was continued for a further 15 min. The reaction mixture was then poured into water (100 ml) and the resulting suspension was extracted with ethyl acetate (2×50 ml). The combined organic extracts were washed with water (2×100 ml), dried and concentrated to give a solid. This was dissolved in a mixture of water (10 ml), THF (10 ml) and glacial acetic acid (10 ml) and heated at reflux for 2 h. After cooling, residual THF was removed in vacuo and the remaining solution was basified (to pH14) by addition of 2N sodium hydroxide. The resulting suspension was extracted with ethyl acetate (2×50 ml) and the combined, dried organic extracts were concentrated onto silica (Merck 7385). FCC eluting with System A (100:8:1) gave the title compound (81 mg) as a solid. The $^1$H-n.m.r. and t.l.c. data obtained for this material were consistent with those obtained for the product of Example 20.

EXAMPLE 23

2,3,4,5-Tetrahydro-5-methyl-2-[(5-methyl-1H-imidazol-4-yl)methyl]-1H-pyrido[4,3-b]indol-1-one 5,6-Dihydro-1-[(5-methyl-1H-imidazol-4-yl)methyl]-4-(2-methyl-2-phenylhydrazino)-2(1H)-pyridinone (20.0 mg) was dissolved in 98% sulphuric acid (1 ml) and the solution was stirred at 25° for 5 min. The mixture was cautiously poured into 8% aqueous sodium bicarbonate solution (60 ml) and extracted with 10% methanol:dichloromethane (2×60 ml). The combined, dried organic extracts were evaporated in vacuo to leave an oil which was purified by FCC eluting with System A (100:8:1) to give the title compound (13.5 mg) as a solid. The $^1$H-n.m.r. and t.l.c. data obtained for this material were consistent with those obtained for the product of Example 20.

EXAMPLE 24

2,3,4,5-Tetrahydro-5-methyl-2-[(5-methyl-1H-imidazol-4-yl)methyl]-1H-pyrido[4,3-b]indol-1-one A solution of N,N,5-trimethyl[-4-[1,2,3,6-tetrahydro-4-[(2-iodophenyl)methylamino]-6-oxo-1-pyridinyl]methyl]-1H-imidazole-1-sulphonamide (264 mg) in a mixture of dioxane and acetonitrile (2:1; 200 ml) containing triethylamine (2 ml) was irradiated in a pyrex immersion well with a medium pressure 125 W mercury lamp at room temperature for 24 h. The reaction mixture was then concentrated onto FCC silica and purified by FCC eluting with System A (150:8:1) to give the title compound (87 mg) as a solid. The $^1$H-n.m.r. and t.l.c. data obtained for this material were consistent with those obtained for the product of Example 20.

EXAMPLE 25

2,3,4,5-Tetrahydro-5-methyl-2-[(5-methyl-1H-imidazol-4-yl)methyl]-1H-pyrido[4,3-b]indol-1-one A solution of N,N,5-trimethyl-4-[(2,3,4,5-tetrahydro-5-methyl-1-oxo-1H-pyrido[4,3-b]indol-2-yl)methyl]-1H-imidazole-1-sulphonamide (86 mg) in 2N hydrochloric acid (10 ml) and absolute ethanol (2 ml) was heated at 100°–110° for 4 h. The reaction mixture was then cooled and 2N sodium hydroxide (50 ml) was added. The resulting solution was extracted with dichloromethane (2×50 ml) and the combined, dried organic extracts were concentrated onto FCC silica and purified by FCC eluting with System A (100:8:1) to give a solid (36 mg). This was taken up in hot ethyl acetate and purified by slow evaporation to give the title compound (12 mg). The $^1$H-n.m.r. and t.l.c. data obtained for this material were consistent with those obtained for the product of Example 20.

EXAMPLE 26

2,3,4,5-Tetrahydro-5-methyl-2-[(5-methyl-1H-imidazol-4-yl)methyl]-1H-pyrido[4,3-b]indol-1-one A solution of N,N,5-trimethyl-4-[(2,3,4,5-tetrahydro-5-methyl-1-oxo-1H-pyrido[4,3-b]indol-2-yl)methyl]-1H-imidazole-1-sulphonamide (401 mg) in a mixture of dioxane (150 ml) and acetonitrile (150 ml) containing triethylamine (1 ml) was irradiated at room temperature with a medium pressure mercury lamp for 24 h. The reaction mixture was then concentrated in vacuo onto FCC silica and purified by FCC eluting with System A (100:8:1) to give the title compound (203 mg) as a solid. The $^1$H-n.m.r. and t.l.c. data obtained for this material were consistent with those obtained for the product of Example 20.

EXAMPLE 27

2,3,4,5-Tetrahydro-5-methyl-2-[(5-methyl-1H-imidazol-4-yl)methyl]-1H-pyrido[4,3-b]indol-1-one A solution of phenylmethyl 5-methyl-4-[(2,3,4,5-tetrahydro-5-methyl-1-oxo-1H-pyrido[4,3-b]indol-2-yl)methyl]-1H-imidazole-1-carboxylate (134 mg) in a mixture of absolute ethanol and 2N hydrochloric acid (2:1; 30 ml) was heated on a steam bath for 15 min. After cooling, the solution was concentrated in vacuo to ca. 20 ml and diluted with water (40 ml). The mixture was then washed with ethyl acetate (2×40 ml) and the acidic aqueous layer was basified with potassium carbonate solution. The solution was then extracted with ethyl acetate (3×50 ml) and the combined, dried organic extracts, were concentrated onto FCC silica and purified by FCC eluting with System A (150:8:1) to give a solid. This was dissolved in hot methanol and triturated with ether to give the title compound (69 mg). The $^1$H-n.m.r. and t.l.c. data obtained for this material were consistent with those obtained for the product of Example 20.

EXAMPLE 28

2,3,4,5-Tetrahydro-5-methyl-2-[(5-methyl-1H-imidazol-4-yl)methyl]-1H-pyrido[4,3-b]indol-1-one A solution of 2,3,4,5-tetrahydro-2-[[1-(methoxymethyl)-5-methyl-1H-imidazol-4-yl]methyl]-5-methyl-1H-pyrido[4,3-b]indol-1-one and 2,3,4,5-tetrahydro-2-[[1-(methoxymethyl)-4-methyl-1H-imidazol-5-yl]methyl]-5-methyl-1H-pyrido[4,3-b]indol-1-one (34 mg) in 49% hydrobromic acid (2 ml) was heated on a steam bath for ca. 3 h. After cooling, the reaction mixture was basified by addition of potassium carbonate solution and extracted with ethyl acetate (3×50 ml). The combined, dried organic extracts were concentrated in vacuo to give the title compound (6 mg) as a solid. The $^1$H-n.m.r. and t.l.c. data obtained for this material were consistent with those obtained for the product of Example 20.

EXAMPLE 29

2,3,4,5-Tetrahydro-5-methyl-2-[(5-methyl-1H-imidazol-4-yl)methyl]-1H-pyrido[4,3-b]indol-1-one A mixture of 2,3,4,5-tetrahydro-5-methyl-2-[(4-methyloxazol-5-yl)methyl]-1H-pyrido[4,3-b]indol-1-one (100 mg) in formamide (20 ml) was heated at 180° for 24 h. The mixture was then cooled, diluted with water (100 ml) and extracted with dichloromethane (3×100 ml). The combined organic extracts were concentrated in vacuo and the residue was purified by FCC eluting with System A (100:8:1) to give the title compound (40 mg) as a solid. The $^1$H-n.m.r. and t.l.c. data for this material were consistent with those obtained for the product of Example 20.

EXAMPLE 30

2,3,4,5-Tetrahydro-5-methyl-2-[(5-methyl-1H-imidazol-4-yl)methyl]-1H-pyrido[4,3-b]indol-1-one A solution of 4-[[[(1-methyl-1H-indol-2-yl)ethyl]amino]methyl]-N,N,5-trimethyl-1H-imidazole-1-sulphonamide (140 mg) in dry dichloromethane (15 ml) was cooled to 5° and the mixture was stirred under nitrogen while phosgene (12% w/w solution in toluene; 1 ml) was added dropwise. The reaction mixture was stirred at room temperature for 2 h, aluminium trichloride (60 mg) was powdered and added, and stirring was continued overnight. After this time methanol (1 ml) was added and the reaction mixture was adsorbed onto FCC silica and purified by FCC eluting with System A (150:8:1) to give the protected derivative of the title compound (42 mg), as a solid, identical (by t.l.c. and m.p.) to the product of Intermediate 27. Deprotection as described in either of Examples 25 or 26 gives the title compound.

EXAMPLE 31

2,3,4,5-Tetrahydro-5-methyl-2-[(5-methyl-1H-imidazol-4-yl)methyl]-1H-pyrido[4,3-b]indol-1-one A mixture of 4-[[[(3-iodo-1-methyl-1H-indol-2-yl)ethyl]amino]methyl]-N,N,5-trimethyl-1H-imidazole-1-sulphonamide (70 mg), triphenylphosphine (52 mg) and palladium acetate (22 mg) in tri-n-butylamine (5 ml) and dry THF (1 ml) was heated under an atmosphere of carbon monoxide at 120° for 1 h. After cooling the reaction mixture was poured into 2N hydrochloric acid (50 ml) and the resulting mixture was extracted with ethyl acetate (2×50 ml; discarded). The acidic solution was then basified with 2N potassium carbonate and the resulting basic suspension was extracted with ethyl acetate (2×50 ml). The combined, dried organic extracts were concentrated in vacuo to give an oil and residual tri-n-butylamine was removed by distillation to leave a solid. This was adsorbed onto FCC silica and purified by FCC eluting with System A (150:8:1) to give the protected derivative of the title compound (21 mg) as a solid, identical (by t.l.c. and m.p.) to the product of Intermediate 27. Deprotection as described in either of Examples 25 or 26 gives the title compound.

EXAMPLE 32

2,3,4,5-Tetrahydro-5-methyl-2-[(5-methyl-1H-imidazol-4-yl)methyl]-1H-pyrido[4,3-b]indol-1-one 5,6-Dihydro-1-[(5-methyl-1H-imidazol-4-yl)methyl]-4-(2-methyl-2-phenylhydrazino)-2(1H)-pyridinone (60 mg) was dissolved in glacial acetic acid (4 ml). Anhydrous zinc chloride (600 mg) was added, and the mixture was heated at 85° for 1.5 h. The cooled mixture was poured into 8% aqueous sodium bicarbonate solution (100 ml) and extracted with ethyl acetate:methanol (10:1) (2×100 ml). The combined, dried organic extracts were evaporated in vacuo to leave a solid which was purified by FCC eluting with System A (100:8:1) to give the title compound (26 mg). The $^1$H-n.m.r. and t.l.c. data obtained for this material were consistent with those obtained for the product of Example 20.

The following examples illustrate pharmaceutical formulations according to the invention, containing 2,3,4,5-tetrahydro-5-methyl-2-[(5-methyl-1H-imidazol-1-yl)methyl]-1H-pyrido[4,3-b]indol-1-one as the active ingredient. Physiologically acceptable salts and/or solvates of this compound, and other compounds of formula (I) and their physiologically acceptable salts and/or solvates may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Direct Compression Tablet | mg/tablet |
|---|---|
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3tablet machine fitted with 5.5 mm, flat bevelled edge punches.

| Sub-Lingual Tablet | mg/tablet |
|---|---|
| Active Ingredient | 0.5 |
| Compressible Sugar NF | 64.5 |
| Magnesium Stearate BP | 0.5 |
| Compression Weight | 65.0 |

The active ingredient is sieved through a suitable sieve, blended with the excipients and compressed using suitable punches. Tablets of other strengths may be prepared by altering either the ratio of active ingredient to excipients or the compression weight and using punches to suit.

| Wet Granulation Conventional Tablet | mg/tablet |
|---|---|
| Active Ingredient | 0.5 |
| Lactose BP | 153.5 |
| Starch BP | 30.0 |
| Pregelatinised Maize Starch BP | 15.0 |
| Magnesium Stearate BP | 1.5 |
| Compression Weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

| Sub-Lingual Tablet | mg/tablet |
|---|---|
| Active Ingredient | 0.5 |
| Mannitol BP | 58.5 |
| Hydroxypropylmethylcellulose | 5.0 |
| Magnesium Stearate BP | 1.0 |
| Compression Weight | 65.0 |

The active ingredient is sieved through a suitable sieve and blended with the mannitol and hydroxypropylmethylcellulose. Suitable volumes of purified water are added and the powders are granulated. After drying, the granules are screened and blended into tablets using suitable punches.

Tablets of other strengths may be prepared by altering the ratio of active ingredient to mannitol or the compression weight and punches to suit.

| tablet | mg/tablet |
|---|---|
| Active Ingredient | 0.5 |
| *Starch 1500 | 98.5 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitabled machinery. Other doses may be prepared by altering the fill weight an if necessary changing the capsule size to suit.

SYRUP

This may be either a sucrose or sucrose free presentation.

| A. Sucrose Syrup | | mg/5 ml dose |
|---|---|---|
| Active Ingredient | | 0.5 |
| Sucrose BP | | 2750.0 |
| Glycerine BP | | 500.0 |
| Buffer | | |
| Flavour | | |
| Colour | } | as required |
| Preservative | | |
| Purified Water BP | to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
|---|---|
| Active Ingredient | 0.5 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

| INJECTION FOR INTRAVENOUS ADMINISTRATION | | |
|---|---|---|
| | mg/ml | |
| Active Ingredient | 0.05 | 0.5 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

| METERED DOSE PRESSURISED AEROSOL | | |
|---|---|---|
| Suspension Aerosol | mg/metered dose | Per can |
| Active Ingredient micronised | 0.050 | 12.0 mg |
| Oleic Acid BP | 0.020 | 4.80 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminium aerosol cans and suitable metering valves, delivering 85 mg of suspension are crimped onto the cans and the dichlorodifluoromethane is pressure filled into the cans through the valves.

| Solution Aerosol | | |
|---|---|---|
| | mg/metered dose | Per can |
| Active Ingredient | 0.05 | 12.0 mg |
| Ethanol BP | 7.500 | 1.80 g |

| Solution Aerosol (continued) | | |
|---|---|---|
| | mg/metered dose | Per can |
| Trichlorofluoromethane BP | 18.875 | 4.53 g |
| Dichlorodifluoromethane BP | 48.525 | 11.65 g |

Oleic acid BP, on a suitable surfactant e.g. Span 85 (sorbitan trioleate) may also be included).

The active ingredient is dissolved in the ethanol together with the oleic acid or surfactant if used. The alcoholic solution is metered into suitable aerosol containers followed by the trichlorofluoromethane. Suitable metering valves are crimped onto the containers and dichlorodifluoromethane is pressure filled into them through the valves.

| Inhalation Cartridges | |
|---|---|
| | mg/cartridge |
| Active Ingredient (micronised) | 0.05 |
| Lactose BP to | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler.

| SUPPOSITORY | |
|---|---|
| Active Ingredient | 0.5 mg |
| *Witepsol H15 to | 1.0 g |

*Witepsol H15 is a proprietary grade of Adeps Solidus Ph. Eur.

A suspension of the active ingredient is prepared in the molten Witepsol and filled, using suitable machinery, into 1g size suppository moulds.

We claim:

1. A compound of formula (I)

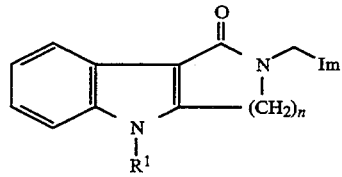

wherein Im represents an imidazolyl group of the formula:

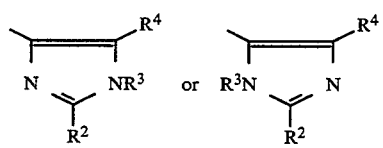

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl $C_{1-4}$alkyl, phenyl, phenyl$C_{1-3}$alkyl, phenylmethoxymethyl, phenoxyethyl phenoxymethyl;

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

n represents 2 or 3;

or a physiologically acceptable salt or solvate thereof.

2. A compound according to claim 1 in which $R^1$ represents a $C_{1-4}$alkyl, $C_{3-4}$alkynyl, $C_{5-6}$cycloaklyl, $C_{5-6}$cycloalkylmethyl, phenyl$C_{1-2}$alkyl, or phenylmethoxymethyl.

3. A compound according to claim 1 in which $R^2$, $R^3$ and $R^4$ each independently represent a hydrogen atom or a $C_{1-3}$alkyl group.

4. A compound according to claim 1 in which $R^1$ represents a hydrogen atom or a $C_{1-4}$alkyl, $C_{3-4}$alkenyl, $C_{3-4}$alkynyl, $C_{5-6}$cycloaklyl, $C_{5-6}$cycloalkylmethyl, phenyl$C_{1-2}$alkyl, or phenylmethoxymethyl, $R^2$ represents a hydrogen atom; and $R^3$ and $R^4$ each represent a hydrogen atom or a $C_{1-3}$alkyl group.

5. A compound according to claim 1 in which $R^1$ represents a methyl, n-propyl, prop-2-ynyl, cyclopentyl, cyclopentylmethyl, or benzyl; $R^2$ and $R^3$ each represent a hydrogen atom; and $R^4$ represents a methyl group.

6. A compound according to claim 4 in which n represents 2.

7. A compound according to claim 5 in which n represents 2.

8. 2,3,4,5-Tetrahydro-5-methyl-2-[(5-methyl-1H-imidazol-4-yl)methyl]-1H-pyrido[4,3-b]indol-1-one; or a physiologically acceptable salt or solvate thereof.

9. A compound selected from:
2,3,4,5-Tetrahydro-5-(phenylmethyl)-2-[(5-methyl-1H-imidazol-4-yl)methyl]-1H-pyrido[4,3-b]indol-1-one;
5-cyclopentyl-2,3,4,5-tetrahydro-2-[(5-methyl-1H-imidazol-4-yl)methyl]-1H-pyrido[4,3-b]indol-1-one;
2,3,4,5-tetrahydro-2-[(5-methyl-1H-imidazol-4-yl)methyl]-5-propyl-1H-pyrido[4,3-b]indol-1-one;
5-(cyclopentylmethyl)-2,3,4,5-tetrahydro-2-[(5-methyl-1H-imidazol-4-yl)methyl]-1H-pyrido[4,3-b]indol-1one;
3,4,5,6-tetrahydro-6-methyl-2-[(5-methyl-1H-imidazol-4-yl)methyl]-azepino[4,3-b]indol-1(2H)-one;
2,3,4,5-tetrahydro-N,N-dimethyl-2-[(5-methyl-1H-imidazol-4-yl)methyl]-1-oxo-5H-pyrido[4,3-b]indole-5-carboxamide;
2,3,4,5-tetrahydro-2-[(5-methyl-1H-imidazol-4-yl)methyl-5-(2-propynyl)-1H-pyrido[4,3-b]indol-1-one;
or a physiologically acceptable salt and solvate thereof.

10. A compound according to claim 1 in the form of a hydrochloride, hydrobromide, sulphate, alkylsulphonate, arylsulphonate, phosphate, acetate, citrate, succinate, tartrate, fumarate or maleate salt.

11. The compound of claim 8 in the form of a hydrochloride salt.

12. The compound of claim 8 in the form of a maleate salt.

13. A pharmaceutical composition which comprises an effective amount of a compound of formula (I) as defined in claim 1 or a physiologically acceptable salt or solvate thereof together with at least one physiologically acceptable carrier or excipient.

14. A pharmaceutical composition according to claim 13 in a form adapted for oral or parenteral administration.

15. A pharmaceutical composition according to claim 13 wherein the active ingredient is 2,3,4,5- tetrahydro-5-methyl-2-[(5-methyl-1H-imidazol-4-yl)methyl]-1H-pyrido[4,3-b]indol-1-one or a physiologically acceptable salt or solvate thereof.

16. A pharmaceutical composition according to claim 13 wherein the active ingredient is 2,3,4,5-tetrahydro-5-methyl-2-[(5-methyl-1H-imidazol-4-yl)methyl-1H-pyrido[4,3-b]indol-1-one hydrochloride.

17. A method of treating a condition which is ameliorated by antagonism of $5HT_3$ receptors which comprises administering to a patient an effective amount of a compound of formula (I) as defined in claim 1 or a physiologically acceptable salt or solvate thereof to relieve said condition.

18. A method according to claim 17 wherein the compound of formula (I) is 2,3,4,5-tetrahydro-5-methyl-2-[(5-methyl-1H-imidazol-4-yl)methyl]-1H-pyrido[4,3-b]indol-1-one or a physiologically acceptable salt or solvate thereof.

19. A method according to claim 17 wherein the compound of formula (I) is 2,3,4,5-tetrahydro-5-methyl-2-[(5-methyl-1H-imidazol-4-yl)methyl]-1H-pyrido[4,3-b]indol-1-one hydrochloride.

20. A method according to claim 17 wherein the condition which is ameliorated by antagonism of $5HT_3$ receptors is anxiety.

21. A method according to claim 20 wherein the compound of formula (I) is 2,3,4,5-tetrahydro-5-methyl-2-[(5-methyl-1H-imidazol-4-yl)methyl]-1H-pyrido[4,3-b]indol-1-one or a physiologically acceptable salt or solvate thereof.

22. A method according to claim 20 wherein the compound of formula (I) is 2,3,4,5-tetrahydro-5-methyl-2-[(5-methyl-1H-imidazol-4-yl)methyl]-1H-pyrido[4,3-b]indol-1-one hydrochloride.

23. A method according to claim 17 wherein the condition which is ameliorated by antagonism of $5HT_3$ receptors is schizophrenia.

24. A method according to claim 23 wherein the compound of formula (I) is 2,3,4,5-tetrahydro-5-methyl-2-[(5-methyl-1H-imidazol-4-yl)methyl]-1H-pyrido[4,3-b]indol-1-one or a physiologically acceptable salt or solvate thereof.

25. A method according to claim 23 wherein the compound of formula (I) is 2,3,4,5-tetrahydro-5-methyl-2-[(5-methyl-1H-imidazol-4-yl)methyl]-1H-pyrido[4,3-b]indol-1-one hydrochloride.

26. A compound according to claim 1 which is 5-ethyl-2,3,4,5-tetrahydro-2-[(5-methyl-1H-imidazol-4-yl)methyl]-1H-pyrido[4,3-b]indol-1-one or a physiologically acceptable salt or solvate thereof.

27. A method according to claim 17 for the treatment of irritable bowel syndrome.

28. A method according to claim 27 wherein the compound of formula (I) is 2,3,4,5-tetrahydro-5-methyl-2-[(5-methyl-1H-imidazol-4-yl)methyl]-1H-pyrido[4,3-b]indol-1-one or a physiologically acceptable salt or solvate thereof.

29. A method according to claim 27 wherein the compound of formula (I) is 2,3,4,5-tetrahydro-5-methyl-2-[(5-methyl-1H-imidazol-4-yl)methyl]-1H-pyrido[4,3-b]indol-1-one hydrochloride.

30. A method according to claim 17 wherein the condition which is ameliorated by antagonism of $5HT_3$ receptors is dyspepsia.

31. A method according to claim 30 wherein the compound of formula (I) is 2,3,4,5-tetrahydro-5-methyl-2-[(5-methyl-1H-imidazol-4-yl)methyl]-1H-pyrido[4,3-b]indol-1-one or a physiologically acceptable salt or solvate thereof.

32. A method according to claim 30 wherein the compound of formula (I) is 2,3,4,5-tetrahydro-5-methyl-2-[(5-methyl-1H-imidazol-4-yl)methyl]-1H-pyrido[4,3-b]indol-1-one hydrochloride.

33. A method according to claim 17 wherein the condition which is ameliorated by antagonism of 5-HT$_3$ receptors is reflux oesophagitis.

34. A method according to claim 33 wherein the compound of formula (I) is 2,3,4,5-tetrahydro-5-methyl-2[(5-methyl-1H-imidazol-4-yl)methyl]-1H-pyrido[4,3-b]indol-1-one or a physiologically acceptable salt or solvate thereof.

35. A method according to claim 33 wherein the compound of formula (I) is 2,3,4,5-tetrahydro-5-methyl-2[(5-methyl-1H-imidazol-4-yl)methyl]-1H-pyrido[4,3-b]indol-1-one hydrochloride.

* * * * *